US009949930B2

(12) United States Patent
Breder et al.

(10) Patent No.: US 9,949,930 B2
(45) Date of Patent: *Apr. 24, 2018

(54) OPIOID AGONIST FORMULATIONS WITH RELEASABLE AND SEQUESTERED ANTAGONIST

(71) Applicant: Purdue Pharma L.P., Stamford, CT (US)

(72) Inventors: Christopher Breder, Greenwhich, CT (US); Curtis Wright, Norwalk, CT (US); Benjamin Oshlack, New York, NY (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/333,584

(22) Filed: Jul. 17, 2014

(65) Prior Publication Data

US 2015/0110879 A1    Apr. 23, 2015

Related U.S. Application Data

(63) Continuation of application No. 13/953,033, filed on Jul. 29, 2013, now Pat. No. 8,815,287, which is a continuation of application No. 13/535,605, filed on Jun. 28, 2012, now Pat. No. 8,518,443, which is a continuation of application No. 13/043,134, filed on Mar. 8, 2011, now Pat. No. 8,231,901, which is a continuation of application No. 10/213,919, filed on Aug. 6, 2002, now Pat. No. 7,914,818.

(60) Provisional application No. 60/310,536, filed on Aug. 6, 2001.

(51) Int. Cl.

| A61K 9/20 | (2006.01) |
|---|---|
| A61K 9/16 | (2006.01) |
| A61K 9/50 | (2006.01) |
| A61K 31/44 | (2006.01) |
| A61K 31/445 | (2006.01) |
| A61K 31/485 | (2006.01) |
| A61K 31/46 | (2006.01) |
| A61K 45/06 | (2006.01) |
| A61K 9/14 | (2006.01) |
| A61K 47/32 | (2006.01) |
| A61K 47/38 | (2006.01) |

(52) U.S. Cl.

CPC ............. *A61K 9/2077* (2013.01); *A61K 9/14* (2013.01); *A61K 9/167* (2013.01); *A61K 9/1635* (2013.01); *A61K 9/1647* (2013.01); *A61K 9/2009* (2013.01); *A61K 9/2013* (2013.01); *A61K 9/2027* (2013.01); *A61K 9/2054* (2013.01); *A61K 9/2081* (2013.01); *A61K 9/2086* (2013.01); *A61K 9/5078* (2013.01); *A61K 9/5084* (2013.01); *A61K 31/44* (2013.01); *A61K 31/445* (2013.01); *A61K 31/46* (2013.01); *A61K 31/485* (2013.01); *A61K 45/06* (2013.01); *A61K 47/32* (2013.01); *A61K 47/38* (2013.01); *A61K 9/5026* (2013.01)

(58) Field of Classification Search
None
See application file for complete search history.

(56) References Cited

U.S. PATENT DOCUMENTS

| 2,770,569 | A | 11/1956 | Fromherz et al. |
|---|---|---|---|
| 3,332,950 | A | 7/1967 | Blumberg et al. |
| 3,493,657 | A | 2/1970 | Lewenstein et al. |
| 3,676,557 | A | 7/1972 | Lachman et al. |
| 3,773,955 | A | 11/1973 | Pachter et al. |
| 3,845,770 | A | 11/1974 | Theeouwes et al. |
| 3,879,555 | A | 4/1975 | Pachter et al. |
| 3,916,889 | A | 11/1975 | Russell |
| 3,965,256 | A | 6/1976 | Leslie |
| 3,966,940 | A | 6/1976 | Pachter et al. |
| 4,063,064 | A | 12/1977 | Saunders et al. |
| 4,088,864 | A | 5/1978 | Theeuwes et al. |
| 4,176,186 | A | 11/1979 | Goldberg et al. |
| 4,237,140 | A | 12/1980 | Dudzinski |
| 4,293,539 | A | 10/1981 | Ludwig et al. |
| 4,366,310 | A | 12/1982 | Leslie |
| 4,401,672 | A | 8/1983 | Portoghese et al. |
| 4,443,428 | A | 4/1984 | Oshlack et al. |
| 4,451,470 | A | 5/1984 | Ganti |
| 4,457,933 | A | 7/1984 | Gordon et al. |
| 4,464,378 | A | 8/1984 | Hussain et al. |
| 4,573,995 | A | 3/1986 | Chen et al. |

(Continued)

FOREIGN PATENT DOCUMENTS

| DE | 2222039 | 11/1972 |
|---|---|---|
| DE | 4325465 | 2/1995 |

(Continued)

OTHER PUBLICATIONS

Kao et al., Abuse-Resistant Opioid Dosage Form, File date: May 11, 2001, Pub. Date:Jan. 2, 2003, US 2003/0004177.

(Continued)

*Primary Examiner* — Bethany P Barham
*Assistant Examiner* — Ping Cao
(74) *Attorney, Agent, or Firm* — Davidson, Davidson & Kappel, LLC

(57) ABSTRACT

Disclosed are oral dosage forms, comprising (i) a therapeutically effective amount of an opioid agonist; (ii) an opioid antagonist in releasable form; and (iii) a sequestered opioid antagonist which is not released when the dosage form is administered intact, and methods thereof.

17 Claims, No Drawings

(56) References Cited

U.S. PATENT DOCUMENTS

| | | | |
|---|---|---|---|
| 4,582,835 A | 4/1986 | Lewis et al. |
| 4,587,118 A | 5/1986 | Hsiao |
| 4,608,376 A | 8/1986 | Pasternak |
| 4,661,492 A | 4/1987 | Lewis et al. |
| 4,719,215 A | 1/1988 | Goldberg |
| 4,730,048 A | 3/1988 | Portoghese et al. |
| 4,760,069 A | 7/1988 | Rzeszotarski et al. |
| 4,769,372 A | 9/1988 | Kreek et al. |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack et al. |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlack |
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,440 A | 7/1993 | London et al. |
| 5,226,331 A | 7/1993 | Thompson et al. |
| 5,236,714 A | 8/1993 | Lee et al. |
| 5,256,669 A | 10/1993 | Askanazi et al. |
| 5,266,331 A | 11/1993 | Oshlak et al. |
| 5,273,760 A | 12/1993 | Oshlak et al. |
| 5,286,493 A | 2/1994 | Oshlak et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlak et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlak et al. |
| 5,356,900 A | 10/1994 | Bihari et al. |
| 5,376,662 A | 12/1994 | Ockert |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,876 A | 12/1996 | Crain et al. |
| 5,585,348 A | 12/1996 | Crain et al. |
| 5,591,452 A | 1/1997 | Miller et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,703,101 A | 12/1997 | Rose et al. |
| 5,763,452 A | 6/1998 | Miller et al. |
| 5,767,125 A | 6/1998 | Crain et al. |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,935,975 A | 8/1999 | Rose et al. |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,954 A | 10/1999 | Foss |
| 5,998,434 A | 12/1999 | Mitch et al. |
| 6,004,970 A | 12/1999 | O'Malley et al. |
| RE36,547 E | 2/2000 | Crain et al. |
| 6,024,982 A | 2/2000 | Oshlack et al. |
| 6,068,855 A | 5/2000 | Leslie et al. |
| 6,077,532 A | 5/2000 | Malkowska et al. |
| 6,077,533 A | 6/2000 | Oshlack et al. |
| 6,103,258 A | 8/2000 | Simon |
| 6,103,261 A | 8/2000 | Chasin et al. |
| 6,120,806 A | 9/2000 | Whitmire |
| 6,143,322 A | 11/2000 | Sackler et al. |
| 6,143,328 A | 11/2000 | Heafield et al. |
| 6,162,467 A | 12/2000 | Miller et al. |
| 6,210,714 B1 | 4/2001 | Oshlack et al. |
| 6,228,863 B1 * | 5/2001 | Palermo ............ A61K 31/44 514/282 |
| 6,254,887 B1 | 7/2001 | Miller et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,326,027 B1 | 12/2001 | Miller et al. |
| 6,335,033 B2 | 1/2002 | Oshlack et al. |
| 6,375,957 B1 | 4/2002 | Kaiko et al. |
| 6,387,404 B2 | 5/2002 | Oshlack et al. |
| 6,399,096 B1 | 6/2002 | Miller et al. |

(56) References Cited

U.S. PATENT DOCUMENTS

| | | |
|---|---|---|
| 6,475,494 B2 | 11/2002 | Kaiko et al. |
| 6,552,031 B1 | 4/2003 | Burch et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,765,010 B2 | 7/2004 | Crain et al. |
| 6,902,742 B2 | 6/2005 | Devane et al. |
| 7,144,587 B2 | 12/2006 | Oshlack et al. |
| 7,172,767 B2 | 2/2007 | Kaiko et al. |
| 7,332,182 B2 | 2/2008 | Sackler |
| 7,658,939 B2 | 2/2010 | Oshlack et al. |
| 7,682,632 B2 | 3/2010 | Oshlack et al. |
| 7,718,192 B2 | 5/2010 | Oshlack et al. |
| 7,914,818 B2 * | 3/2011 | Breder et al. .......... 424/468 |
| 8,231,901 B2 * | 7/2012 | Breder et al. .......... 424/464 |
| 8,518,443 B2 * | 8/2013 | Breder et al. .......... 424/464 |
| 8,815,287 B2 * | 8/2014 | Breder et al. .......... 424/464 |
| 2002/0058673 A1 | 5/2002 | Kaiko et al. |
| 2003/0004177 A1 | 1/2003 | Kao et al. |
| 2003/0064099 A1 | 4/2003 | Oshlack et al. |
| 2003/0068371 A1 | 4/2003 | Oshlack et al. |
| 2003/0069263 A1 | 4/2003 | Breder et al. |
| 2003/0157168 A1 | 8/2003 | Breder et al. |
| 2003/0191147 A1 | 10/2003 | Sherman et al. |
| 2004/0092542 A1 | 5/2004 | Oshlack et al. |
| 2004/0131552 A1 | 7/2004 | Boehm |
| 2004/0186121 A1 | 9/2004 | Oshlack et al. |
| 2004/0192715 A1 | 9/2004 | Chasin et al. |
| 2004/0228924 A1 | 11/2004 | Oshlack et al. |
| 2005/0095291 A1 | 5/2005 | Oshlack et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0245557 A1 | 11/2005 | Choenhard et al. |
| 2006/0039970 A1 | 2/2006 | Oshlack et al. |
| 2006/0182801 A1 | 8/2006 | Breder et al. |
| 2007/0014732 A1 | 1/2007 | Sackler |
| 2007/0122348 A1 | 5/2007 | Kaiko et al. |
| 2008/0020028 A1 | 1/2008 | Shevchuk et al. |
| 2010/0151014 A1 | 5/2010 | Liang et al. |
| 2010/0152221 A1 | 5/2010 | Liang et al. |

FOREIGN PATENT DOCUMENTS

| | | |
|---|---|---|
| DE | 29719704 | 2/1997 |
| DE | 19651551 | 6/1998 |
| EP | 0193355 | 9/1986 |
| EP | 0205282 | 12/1986 |
| EP | 0319243 | 6/1989 |
| EP | 0352361 | 1/1990 |
| EP | 0319243 | 11/1990 |
| EP | 0647448 | 4/1995 |
| EP | 0913152 | 6/1999 |
| EP | 0548448 | 9/2000 |
| WO | WO/8303197 | 9/1983 |
| WO | WO/8701282 | 3/1987 |
| WO | WO/9004965 | 5/1990 |
| WO | WO/9406426 | 3/1994 |
| WO | WO/9503804 | 2/1995 |
| WO | WO/9602251 | 2/1996 |
| WO | WO/9733566 | 9/1997 |
| WO | WO 9825613 | 6/1998 |
| WO | WO/9835679 | 8/1998 |
| WO | WO/9932119 | 1/1999 |
| WO | WO/9932120 | 7/1999 |
| WO | WO/0001377 | 1/2000 |
| WO | WO/0038649 | 7/2000 |
| WO | WO/0132180 | 5/2001 |
| WO | WO/0137785 | 5/2001 |
| WO | WO/0152851 | 7/2001 |
| WO | WO/0168080 | 9/2001 |
| WO | WO/0185257 | 11/2001 |
| WO | WO/0193852 | 12/2001 |
| WO | WO/02092059 | 11/2002 |
| WO | WO/2004052346 | 6/2004 |
| WO | WO/2009/085778 | 7/2009 |

OTHER PUBLICATIONS

Foss, J.F. et al., Abstract, "Prevention of Apomorphine- or Cisplatin-induced emesis in the dog by combination of Methylnaltrexone and morphine" Cancer Chemother Pharmacol (1998); 42(4):287-91.

Yuan et al., Drug and Alcohol Dependence "Efficacy of Orally Administered Methylnaltrexone in Decreasing Subjective Effects After Intravenous Morphine" (1998); 52:161-165.

Gan et al., "Opioid-Sparing Effects of a Low-Dose Infusion of Naloxone in Patient-Administered Morphine Sulfate," Anesthesiology (1997), 87(5):1075-1080.

Shen et al., "Ultra-Low Doses of Naltrexone or Etorphine Increase Morphine's Antinocieceptive Potencey and Attenuate Tolerance/Dependence in Mice," Brain Research (1997), 757:176-190.

Yuan et al., "The Safety and Efficacy of Oral Methylnaltrexone in Preventing Morhpine-induced Delay in Oral-Cecal Transit time", Clinical Trials and Therapeutics (1997), 61:467-475.

Mendelson J., et al, "Buprenorphine and Naloxone Interactions in Opiate Dependent Volunteers," Clin. Phar. Ther. (1996), 60:105-114.

Walsh et al., "Effects of Naltrexone on Response to Intravenous Cocain, Hydromorphone and their Combination in Humans," (1996).

Chih-Cheng Chien, et al., "Sigma antagonists potentiate opioid analgesia in rats", Neuroscience Letters 190 (1995), 137-139.

Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.

Hanson, Analgesic, Antipyretic and Anti-Inflammatory Drugs in Remington's Science and Practice of Pharmacy (1995), 2:1207.

Talwin Nx, Physician's Desk Reference 48.sup.th Ed. (1994) Montvale, NJ 2120-2121.

Foss et al., "Dose related antagonism of the Emetic Effect of Morphine by Methylnaltrexone in dogs", J. Clin Pharmacol (1993), 33:747-751.

Holmes et al., "Inhibiting Spinal Dynorphin A Component Enhances Intrathecal Morphine Antinociception in Mice", Anesth. Analg. (1993), 77:1166-73.

Miakowski et al., "Inhibition of Spinal Opioid Analgesia by Supraspinal Administration of Selective Opioid Antagonists", Brain Research (1992), 30:263-274.

Weinhold et al.,"Buprenorphine Alone and in Combination with Naltrexone in Non-Dependent Humans, Drug and Alcohol Dependence" (1992), 30:263-274.

Cappel et al.,"Enhancement of Naloxone Induced Analgesia by Pretreatment with Morphone", Pharma. Bioch. & Behav.(1989), 34:425-427.

Vaccarino et al.,"Analgesia Produced by Normal Doses of Opioid Antagonists Alone and in Combination With Morphine", Pain (1989), 36:103-109.

Gonzalez et al., "Naltrexone: A Review of its Pharmacodynamic and Pharmacokinetic Properties and Therapeutic Efficacy in the Management of Opioid Dependence," Drugs (1988), 35:192-213.

Sunshine, et al., "Analgesic Efficacy of Pentazocine Versus a Pentazocine-Naloxone Combination Following Oral Administration," Clin. J. Pain (1988), 4:35-40.

Wang et al., "Crossover and Parallel Study of Oral Analgesics," J. Clin. Pharmacol (1981), 21:162-168.

Translation of German patent application DE 43 25 465 published on Feb. 1995.

Alavrez-Fuentes, et al. "Effectiveness of Repeated Administration of a New Ora Naltrexone Controlled-Release System in Morphine Analgesia"; J. Pharm Pharmcaol (2001), 53:1201-1205.

Alvarez-Fuentes, et al., :Preclinical Study of an Oral Controlled Release Naltrexone Complex in Mice; J. Pharm Pharmacol (2000), 52:659-663.

(56) References Cited

OTHER PUBLICATIONS

Archer, Sydney; "Historical Perspective on the Chemistry and Development of Naltrexone"; Naltrexone Research Monograph28 (1980) p. 3-9.
Baum et al., "The Impact of the Addition of Naloxone on thr Use and Abuse of Pentazocine"; Public Health Reports (1987) vol. 102, No. 4 p. 426-429.
Rapaka et al., "Discovery of Novel Opioid Medications"; NIDA Research Monograph 147 (1995) p. 55-83.
Bloom et al., "Clinical Studies with Naloxone/Methadone in a Ratio of 1:20"; 5.sup.th National Conference on Methadone Treatment (1973) vol. 2, p. 1342-1349.
Blachly, M.D., "Naloxone in opiate Addiction"; Current Psychiatric Therapies (1976) p. 209-213.
Briscoe et al., "Methoclocinnamox: Time Course of Changes in Alfetnanil-Reinforced Rhesus Monkeys"; Psychopharmacology (2000) 148:393-399.
Abstract of Bromm, et al., "A Sensitive Method to Evaluate Effects of Analgesics in Man"; Meth and Find Exptl Clin Pharmacol 5 (8) (1983) p. 545-551.
Bullingham et al., "Clinical Pharamcokinetics of Narcotic Agonist-Antagonist Drugs"; Clinical Pharm (1983) 8: 332-343.
Calimlim, et al. "Effect of Naloxone on the Analgesic Activity of Methadone in a 1:10 Oral Combination"; Clin Pharmacol and There (1974) vol. 15; No. 6 pp. 556-564.
Caruso et al., "Methadone and Naloxone in Combination (Naldone. RTM.) for the Treatment if Heroin Addicts"; Bristol Laboratories, pp. 1336-1341F (1973).
Chemy, Nathan I., "Opioid Analgesics"; Drugs May 1996:51 (5) pp. 713-737.
Chiang, et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacol Thera (1984) vol. 36 No. 5, pp. 704-708.
Comer et al., "Depot Naltrexone: Long-lasting Antagonism of the Effects of Heroin un Humans"; Psychopharmacology (2002) 159, pp. 351-360.
Crabtree et al., "Review of Naltrexone, a long-acting Opiate Antagonist"; Clinical Pharmacy, vol. 3 (1984) pp. 273-280.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 82 (1999)pp. 1-11.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.
Fink et al., "Naloxone in Heroin Dependence"; Clin Pharm and Thera. vol. 9, No. 5;pp. 568-577 (1968).
Fishman et al., "Disposition of Naloxone-7,8.sup.3H in Normal & Narcotic Dependent Men"; J. Pharm. and Exper. Thera (1973)vol. 10 No. 2;pp. 575-580.
Fraser, Albert D., et al., "Clinical Toxicology of Drugs Used in the Treatment of Opiate Dependency"; Clinical Toxicology I(1990) vol. 10, No. 2; pp. 375-386.
Freye et al., "effects of Tramadol and Tilidine/Naloxone on Oral-Caecal Transit & Pupillary light Reflex"; Arznelm-Forsch/Drug Res. 50(I)(2000)pp. 24-30.
Fudala, et al., "Effects of Buprenorphine asnd Naloxone in Morphine-Stabilized Opioid Addicts": Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gerra et al., "Clonidine and Opiate Receptor Antagonists in the Treatment of Heroin Addiction"; J. Substance Abuse Treatment (1995) vol. 12, 1, pp. 35-41.
Ghodse, et al., "Opioid analgesics and Narcotic Antagonists"; Side Effects of Drugs (2000) Annual 23, chpt 8 pp. 96-113.
Glatt, William, M.D. FACP, "A New Method for Detoxifying Opoiod-Dependent Patients"; J. Substance Abuse Treatment (1999) vol. 17, No. 3,pp. 193-197.
Gold, et al. "Rapid Opioid Detoxification During General Anesthesia"; Anesthesiology (1999) vol. 91, No. 6, pp. 1639-1647.
Greenwald, et al., "Comparative Clinical Pharmacology of Short-Acting .mu..upsilon. Opioids in Drug Abusers"; J. Pharm and Exper Thera (1996) vol. 277, No. 3, pp. 1228-1236.
Gupta, et al., :Morphine Combined with Doxapram or Naloxone; Anesthesia (1974) vol. 29, pp. 33-39.
Richter et al., "Clinical Investigation on the Development of Dependence during Oral Therapy with Tramadol"; Arzniem-Forsch/Drug Res. 35 (No. II)(1985)pp. 1742-1744.
Rosen et al., "The effect of Lamotrigine on Naloxone-precipitated Opiate withdrawal"; Drug and Alcohol Dependence (1998) vol. 52, pp. 173-176.
Rosen et al., "A Pilot Study of Dextromethorphan in Naloxone-Precipitated Opiate Withdrawal"; European J. of Pharm. (1996) vol. 307, pp. 251-257.
Schuh et al., "Buprenorphine, Morphine and Naloxone Effects during Ascending Morphine Maintenance in Humans"; J. Pharm Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opiopd Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Precipitated Withdrawal by Pentazocine in Methadone-Maintained Volunteers"; J. Pharm and Exper Thera (1993) vol. 267, No. 2, pp. 624-634.
Tai, et al., "Naltrexone: An Antagonist Therapy for Heroin Addiction"; NIDA (1997) 5 pages.
Umbricht et al., "Naltrexone shortened opioid detoxification with buprenorphine"; Drug and Alcohol Dependence (1999) vol. 56 pp. 181-190.
Vaccarino et al., "Enogenous Opiates: 1999"; Peptides 21 (2000) pp. 1975-2034.
Wang et al., "Inverse Agonists and neutral antagonists at .mu. opioid receptor (MOR): possible role of basal receptor signaling in narcotic dependence"; J. Neurochemistry (2001) vol. 77, pp. 1590-1600.
Way et al., "Responsivity to Naloxone during Morphine Dependence"; Annals New York Academy of Sciences, (1976); pp. 252-261.
Weinberg et al., "Sublingual absorption of selected opioid analgesics"; Clin Pharm Thera (1988) vol. 44, No. 3, pp. 335-342.
Wells, et al., "In vivo Pharmacological Characterization of SoRI 9409, a Nonpeptidic Opioid .mu.-Agonist/.delta.-Antagonist that Produces Limited Antinociceptive Tolerance and Attenuates Morphione Physical Dependence"; J. Pharm and Exper Thera (2001) vol. 297, No. 2, pp. 597-605.
Wodak, Alex, "Drug Treatment for Opioid Dependence"; Australian Prescriber (2001) vol. 24, No. 1, pp. 4-6.
Wright et al., "Acute physical dependence in Humans; repeated naloxone-precipitated withdrawal after a single-dose of methadone"; Drug and Alcohol Dependence (1991) vol. 27, pp. 139-148.

(56) References Cited

OTHER PUBLICATIONS

Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Budd, Keith, "Clinical Use of Opioid Antagonists"; Bailliere's Clinical Anesthesiology (1987) vol. 1, No. 4, pp. 993-1011.
Crain et al., Ultra-low concentrations of naloxone selectively antagonize excitatory effects of morphine on sensory neurons, thereby increasing its antinociceptive potency and attenuating tolerance/dependence (1995).
Howes et al., "The Pharmacology of TR5109, a new Narcotic Agonist/Antagonist Analgesic"; NIDA Research (1979) pp. 99-105.
Leeling et al., "Disposition and metaboliam of codorphone in the rat, dog, and man"; Drug Metabolism and Disposition (1982) vol. 10, No. 6, pp. 649-653.
Amass et al., "Efficacy of daily and alternate-day dosing regimens with the combibation buprenorphine-naloxone tablet"; Drug and Alcohol Dependence (2000) vol. 58, pp. 143-152.
Hassain et al., "Buccal and oral bioavailability of naloxone and naltrexone in rats";(1987) vol. 36, pp. 127-130.
Jasinski et al., "The human pharmacology and abuse potential of N-allylnoroxymorphone naloxone"; J. Pharm and Exper Thera (1967) vol. 157, No. 2, pp. 420-426.
Jones et al., Nalmefene:blockade of intravenous morphine challenge effects in opioid abusinh humans; Drug and Alcohol Dependence (2000) vol. 60, pp. 29-37.
Kanof et al., "Clinical Charateristics of Naloxone-Precipitated Withdrawal in Human Opioid-Dependent Subjects"; J Pharma and Exper Thera (1992), vol. 260, No. 1, pp. 355-363.
King et al, Naltrexone Biotransformation and Incidence of Subjective Side Effects: A Preliminary Study; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. in Chem. Path. and Pharm (1977) vol. 18, No. 1, pp. 29-34.
Kosten, Thomas R., M.D.,"Buprenorphine for Benzodiazepine-Abusing Heroin Addicts"; Amer J of Phsychiatry (1994) vol. 1, p. 151.
Kosten et al., "Opioid antagonist challenges in buprenorphine maintained patients"; Drug and Alcohol Dependence (1990) vol. 25, OO. 73-78.
Kurland et al., "Naloxone and the Narcotic Abuser: A Controlled Study of Partial Blockade"; Inter. J. of the Addictions (1974) vol. 9, No. 5, pp. 663-672.
Lee et al., "Nalbuphine Coadministered with Morphine Prevents Tolerance and Dependence"; Anesth Analg (1997) vol. 84, pp. 810-815.
Lehman, et al.,"Influence of Naloxone on the Postoperative Analgesic and Respiratory effects of Buprenorphine"; Eur. J. Clin Pharm (1988) vol. 34, pp. 343-352.
Levine et al., "Potentiation of Pentazocine Analgesia by Low-dose Naloxone"; J Clin Invest (1988) vol. 82, pp. 1574-1577.

Loimer et al., "Combined Naloxone/Methadone Preparations for Opiate Substitution Therapy"; J. of Substance Abuse Treatment (1991) vol. 8, pp. 157-160.
Martin et al. "Bioavailability Investigation of a New Tilidine/Naloxone Liquid Formulation Compared to a Reference Formulation"; Arzneim-Forsch./Drug Res. (1999) vol. 49, pp. 599-607.
Martin et al., "Demonstration of Tolerance to and Physical Dependence on N-allynormorphine (Nalorphine)";J. of Pharm and Exper Thera (1965) vol. 150, No. 3. pp. 437-442.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson et al., "Buprenophine and naloxone Interactions in Methadone Maintenance Patients"; Society of Biological Psychiatry (1997) vol. 41, pp. 1095-1101.
Nutt et al., "Methadone-naloxone mixture for use in methadone maintenance programs"; Clin Pharm and Ther. vol. 15, No. 2., pp. 156-166 (1974).
Parwatikar et al., "Methadone-naloxone in combination for the Treatment of Heroin Addicts"; Clin. Pharm and Thera, vol. 14, No. 6, pp. 941-948 (1973).
Parwartikar et al., "Naloxone-Methadone Combination for the Treatment of Opiate Dependence"; Missouri Institute of Psychiatry, pp. 1350-1354 (1973).
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Bigelow et al., "Abuse Liability and Assessment of Buprenorphine-Naloxone Combinations"; Dept of Psychiatry and Behavioral Sciences, The Johns Hopkins University School of Medicine, pp. 145-149. (1987).
Wikler et al., "N-Allylnormorphine: Effects of single dose and Precipitation of Acute "Abstinence Syndromes" during addiction to morphine, methadone or heroin in man (post addicts)"; N-Allylnormorphine During Narcoctic Addiction (1953) pp. 8-20.
Zaks et al., "Naloxone Treatment of Opiate Dependence"; JAMA (1971) vol. 215, No. 13, pp. 2108-2110.
Barton, et al., "Intranasal Administration of Naloxone by Paramdeics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, 524-529.
Jasinski, D.R., "Assessment of the Abuse Poteniality of Morphine-like Drugs (Methods Used in Man)"; Drug Addiction (1977) pp. 197-258.
Johnson et al., "Buprenorphine and Naloxone for Heroin Dependence"; Substance Use Disorders (2000) pp. 519-526.
Strain et al., "Opioid antagonist effects of dezocine in opioid-dependent humans"; Clin Pharm and Thera (1996) vol. 60, No. 2, pp. 206-217.
Preston et al., "Abuse liability and studies of opioid agonist-antagonists in humans"; Drug and Alcohol Dependence (1991) vol. 28, pp. 49-82.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Benfey, "Function of Myocardial .alpha.-Adrenoceptors"; Life Sciences (1982) vol. 31, pp. 101-112.
Levine et al., "Potentiation of Pentazocine Analgesia by Low-dose Naloxone"; J of Clin Invest. (1988) vol. 82, pp. 1547-1577.

(56) References Cited

OTHER PUBLICATIONS

Yoburn et al., Opioid Antagonist-induced Receptor Upregulation: Effects of Concurrent Agonist Administration; Brain Research Bulletin (1994), vol. 33, pp. 237-240.

Bunzow et al., "Molecular Closing and Tissue Distribution of a Putative Member of the Rat Opioid Receptor Gene Family that is not a .mu., .delta., or .kappa. opioid receptor type"; FEBS letters (1994) pp. 284-288.

Mollereau et al., "ORL I, a novelmember of the opioid receptor family: Cloning, functional expression and localization"; FEBS letters 341 (1994),pp. 33-38.

Wang, et al.,"cDNA cloning a=of an orphan opiate receptor gene family member and its splice variant"; FEBS letters 348 (1994) pp. 75-79.

Suzuki et al., "Morphine conditioned place preference after chronic treatment with naloxone in the rat"; Research Communications in Substance Abuse (1991) vol. 12., No. 3., pp. 119-131.

Press Release "International Patent Application to Be Published on Abuse-Resistant Pain Reliever Being Developed by Perdue Pharma"; Aug. 8, 2001.

Paronis et al., "Increased Analgesic Potency of Mu Agonists after Continuous Naloxone Infusion in Rats"; J fo Pharm Exper Thera (1991), 259 (2), pp. 582-589.

Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.

Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.

Zhang et al., "Down-Regulation of .mu.-Opioid Receptors in Rat and Monkey Dorsal Root Ganglion Neurons and Spinal Cord After Peripheral Axotomy"; Neuroscience (1998) vol. 82., pp. 223-240.

Abdulla et al., "Axotomy reduces the effect of analgesic opioids yet increases the effect of nociceptin on dorsal root ganglion neurons"; J of Neuro Sci (1998) vol. 18, pp. 9685-9694.

Di Giannuario et al., Orphanin FQ reduces morphine-induced dopamine release in the nucleus accumbens: a microdialysis study in rats; Neurosci. Lett (1999) vol. 272 pp. 183-186.

Ciccocippo et al., "Effect of Nociceptin/orphanin FQ on the Rewarding Properties of Morphine", Eur. J. Pharmacol (2000) vol. 404, pp. 153-159.

Revia, Physician's Desk Reference 55.sup.th Ed. (2001)Montvale, NJ, pp. 1146-1149.

Executed Employment Agreement of Ben Oshlack, Sep. 5, 1980.

Executed Employment Agreement of J.David Haddox, Aug. 13, 1999.

Executed Employment Agreement of Curtis Wright, Oct. 7, 1998.

Executed Employment Agreement of Christopher D. Breder, Aug. 13, 1999.

Notice of Recordation of Assignment Document dated Feb. 3, 2003, for U.S. Appl. No. 10/213,919 (including the assignment documents).

Notice of Recordation of Assignment Document dated Dec. 13, 2007, for U.S. Appl. No. 10/213,919 (including a the assignment document).

Notice of Recordation of Assignment Document dated May 10, 2001, for U.S. Appl. No. 09/781,081 (including the assignment documents).

Notice of Recordation of Assignment Document dated Aug. 21, 2004, for U.S. Appl. No. 09/781,081 (including a the assignment document).

Notice of Recordation of Assignment Document dated May 11, 2009, for U.S. Appl. No. 10/689,866; U.S. Appl. No. 10/700,861; U.S. Appl. No. 10/700,893; U.S. Appl. No. 10/700,906; U.S. Appl. No. 10/701,041; and U.S. Appl. No. 09/781,081 (including a the assignment document).

Opinion and Order, Civil Action No. 1:08CV00050, Jun. 22, 2010.

Interview Summary issued in connection with U.S. Appl. No. 10/667,676 dated Feb. 12, 2010.

Suggestion for Interference filed in connection with U.S. Appl. No. 10/689,866 dated May 11, 2010.

* cited by examiner

OPIOID AGONIST FORMULATIONS WITH RELEASABLE AND SEQUESTERED ANTAGONIST

This application claims priority from U.S. Provisional Application Ser. No. 60/310,536 filed Aug. 6, 2001, the disclosure of which is hereby incorporated by reference in its entirety.

BACKGROUND OF THE INVENTION

Opioid formulations are sometimes the subject of abuse. A particular dose of oxycodone may be more potent when administered parenterally as compared to the same dose administered orally. Also, some formulations can be tampered with in order to provide the opioid agonist contained therein better available for illicit use. For example, a controlled release opioid agonist formulation can be crushed in order to provide the opioid contained therein available for immediate release upon oral or parenteral administration. An opioid formulation can also be abusable by administration of more than the prescribed dose of the drug.

Opioid antagonists have been combined with certain opioid agonists in order to deter the parenteral abuse of opioid agonists. In the prior art, the combination of immediate release pentazocine and naloxone has been utilized in tablets available in the United States, commercially available as Talwin® Nx from Sanofi-Winthrop. Talwin® Nx contains immediate release pentazocine hydrochloride equivalent to 50 mg base and naloxone hydrochloride equivalent to 0.5 mg base. A fixed combination therapy comprising tilidine (50 mg) and naloxone (4 mg) has been available in Germany for the management of pain since 1978 (Valoron® N, Goedecke). A fixed combination of buprenorphine and naloxone was introduced in 1991 in New Zealand (Temgesic® Nx, Reckitt & Colman) for the treatment of pain.

Purdue Pharma L.P currently markets sustained-release oxycodone in dosage forms containing 10, 20, 40 and 160 mg oxycodone hydrochloride under the tradename OxyContin.

U.S. Pat. Nos. 5,266,331; 5,508,042; 5,549,912 and 5,656,295 disclose sustained release oxycodone formulations.

U.S. Pat. Nos. 4,769,372 and 4,785,000 to Kreek describe methods of treating patients suffering from chronic pain or chronic cough without provoking intestinal dysmotility by administering 1 to 2 dosage units comprising from about 1.5 to about 100 mg of opioid analgesic or antitussive and from about 1 to about 18 mg of an opioid antagonist having little to no systemic antagonist activity when administered orally, from 1 to 5 times daily.

U.S. Pat. No. 6,228,863 to Palermo et al. describes compositions and methods of preventing abuse of opioid dosage forms.

WO99/32119 to Kaiko et al. describes compositions and methods of preventing abuse of opioid dosage forms.

U.S. Pat. No. 5,472,943 to Crain et al. describes methods of enhancing the analgesic potency of bimodally acting opioid agonists by administering the agonist with an opioid antagonist.

All documents cited herein, including the foregoing are incorporated by reference in their entireties for all purposes.

OBJECTS AND SUMMARY OF THE INVENTION

It is an object of the invention to provide an oral dosage form of an opioid agonist that is useful for decreasing the potential for abuse of the opioid agonist contained therein.

It is an object of certain embodiments of the invention to provide an oral dosage form of an opioid agonist that is useful for decreasing the potential abuse of the opioid agonist without affecting the analgesic effects of the opioid agonist or incurring the risk of precipitating withdrawal if taken intact.

It is an object of certain embodiments of the invention to provide an oral dosage form of an opioid agonist that is resistant to misuse, abuse or diversion, wherein said resistance does not depend on individual patient-specific differences in the effects of co-administered opioid agonist and antagonist mixtures.

It is an object of certain embodiments of the invention to provide an oral dosage form containing an effective dose of an opioid agonist along with a dose of opioid antagonist which does not change the analgesic efficacy of the opioid agonist when the dosage form is orally administered intact, but which can prevent abuse if the dosage form is tampered with by interfering with the effect of the opioid agonist.

It is an object of certain embodiments of the invention to provide a method for preventing abuse of an oral opioid dosage form where the dosage form also includes a dose of opioid antagonist which is sequestered, e.g., is not bioavailable when the dose is administered intact but is bioavailable when the dosage form is tampered with (e.g., in an attempt to misuse the dose of opioid analgesic) and a dose of antagonist which is releasable to provide a desired effect.

It is an object of certain embodiments of the invention to provide oral dosage forms that are intended for or are suitable for use in the management of acute or chronic pain where alteration of the opioid agonist's analgesic affects must be avoided such as in cases of tolerance, physical dependence or individual variability in hepatic metabolism or physiology.

It is a further object of a preferred embodiment of the invention to provide a method of treating pain in human patients with an oral dosage form of an opioid agonist while reducing its misuse by oral, parenteral, intranasal and/or sublingual route.

It is an object of certain embodiments of the invention to provide an oral dosage form of an opioid analgesic which is subject to less abuse potential via the oral route than prior commercially available dosage forms.

It is an object of certain embodiments of the present invention to provide an oral dosage form of an opioid analgesic and method which provides therapeutic analgesia and which also provides a negative, "aversive" experience when the prescribed amount or a large amount of the opioid, e.g., about 2-3 times the usually prescribed dose, is taken by or administered to a physically dependent subject.

It is an object of certain embodiments of the present invention to provide an oral dosage form of an opioid analgesic and a method for providing therapeutic analgesia in a manner which is not as positively reinforcing in non-physically dependent subjects taking the same or more than the usually prescribed dose, e.g., about 2-3 times the usually prescribed dose of the opioid, as compared to the same amount of opioid without the antagonist.

It is an object of certain embodiments of the invention to provide a method of treating pain in human patients with an oral dosage form of an opioid analgesic while reducing the oral abuse potential of dosage form.

It is an object of certain embodiments of the invention to provide a method of manufacturing an oral dosage form of an opioid analgesic such that it has less oral abuse potential.

It is an object of certain embodiments of the invention to provide a composition and method of enhancing the analgesic potency of opioid agonists by blocking their anti-analgesic side-effects.

It is an object of certain embodiments of the invention to provide a composition and method of attenuating physical dependence, tolerance, hyperexcitability, hyperalgesia and other undesirable side-effects caused by the chronic administration of opioid agonists.

It is an object of certain embodiments of the invention to provide a composition and method for detoxifying and treating opiate addicts utilizing opioid receptor antagonists.

It is an object of certain embodiments of the invention to provide a composition which enhances the analgesic effects of opioid agonists while simultaneously attenuating undesirable side-effects caused by said opioid agonists, including physical dependence, tolerance, hyperexcitability and hyperalgesia.

Some or all of the above objects are achieved by the present invention which is directed to an oral dosage form, comprising (i) a therapeutically effective amount of an opioid agonist; (ii) an opioid antagonist in releasable form; and (iii) a sequestered opioid antagonist which is not released when the dosage form is administered intact.

Certain embodiments of the invention are directed to an oral dosage form, comprising (i) a first component comprising a therapeutically effective amount of an opioid agonist; (ii) a second component comprising an opioid antagonist in releasable form; and (iii) a third component comprising a sequestered opioid antagonist which is not released when the dosage form is administered intact.

Certain embodiments of the invention are directed to an oral dosage form comprising (i) a first component comprising a therapeutically effective amount of an opioid agonist; (ii) a second component comprising an opioid antagonist in releasable form, and a sequestered opioid antagonist which is not released when the dosage form is administered intact.

Certain embodiments of the invention are directed to an oral dosage form, comprising (i) a first component comprising a therapeutically effective amount of an opioid agonist and an opioid antagonist in releasable form; and (ii) a second component comprising a sequestered opioid antagonist which is not released when the dosage form is administered intact.

Certain embodiments of the invention are directed to an oral dosage form, comprising (i) a first component comprising a therapeutically effective amount of an opioid agonist and an opioid antagonist in releasable form; and (ii) a second component comprising a sequestered opioid antagonist which is not substantially released when the dosage form is administered intact.

Certain embodiments of the invention are directed to an oral dosage form, comprising (i) a first component comprising a therapeutically effective amount of an opioid agonist; (ii) a second component comprising an opioid antagonist in releasable form; and (iii) a third component comprising a sequestered opioid antagonist which is not substantially released when the dosage form is administered intact.

Certain embodiments of the present invention is directed to a dosage form formulated such that the ratio of the amount of antagonist released from the dosage form after tampering to the amount of the antagonist released from the intact dosage form is about 3:1 or greater, based on the in-vitro dissolution at 1 hour of the dosage form in 900 ml of Simulated Gastric Fluid using a USP Type II (paddle) apparatus at 75 rpm at 37 degrees C.

In embodiments of the invention wherein the antagonist in non-releasable form can be in the form of multiparticulates coated with a sequestering material, the multiparticulates can be in the form of inert beads coated with the antagonist and overcoated with the material, or alternatively in the form of a granulation comprising the antagonist and the material. The multiparticulates can be dispersed in a matrix comprising the opioid agonist or contained in a capsule with the opioid agonist.

In embodiments of the invention wherein the antagonist is dispersed in a matrix comprising a sequestering material which substantially prevents the release of the antagonist, the matrix can be in the form of pellets. The pellets can be dispersed in another matrix comprising the opioid agonist or contained in a capsule with the opioid agonist.

In other embodiments of the invention, part of the antagonist is in a matrix and/or part of the antagonist is in a coated bead.

In certain embodiments of the invention which exhibit the above-disclosed ratio of about 3:1 or greater concerning the amount of antagonist released from the dosage form after tampering to the amount of said antagonist released from the intact dosage form based on the dissolution at 1 hour of the dosage form in 900 ml of Simulated Gastric Fluid using a USP Type II (paddle) apparatus at 75 rpm at 37 degrees C., the intact dosage form releases 22.5% or less of the antagonist after 1 hour and the tampered dosage form releases 67.5% or more antagonist after 1 hour. In another embodiment, the intact dosage form releases 20% or less of said antagonist after 1 hour and the tampered dosage form releases 60% or more antagonist after 1 hour. In another embodiment, the intact dosage form releases 10% or less of said antagonist after 1 hour and the tampered dosage form releases 30% or more antagonist after 1 hour. In another embodiment the intact dosage form releases 5% or less of said antagonist after 1 hour and the tampered dosage form releases 15% or more antagonist after 1 hour.

In certain embodiments of the invention, the ratio of the amount of antagonist released from the dosage form after tampering to the amount of said antagonist released from the intact dosage form based on the dissolution at 1 hour of the dosage form in 900 ml of Simulated Gastric Fluid using a USP Type II (paddle) apparatus at 75 rpm at 37 degrees C. is 4:1 or greater, 10:1 or greater, 50:1 or greater or 100:1 or greater.

The invention is also directed to methods of preventing abuse of an opioid agonist utilizing the dosage forms disclosed herein. The method can comprise providing the opioid agonist in an oral dosage form together with an opioid antagonist in non-releasable form upon digestion when the integrity of the dosage form is maintained until digestion begins, but which becomes bioavailable if subjected to tampering (e.g., crushing, shear forces which break up the dosage form, etc., solvents or temperatures of greater than 45° C.).

Another embodiment of the invention is directed to a method of decreasing the abuse of an opioid agonist in an oral dosage form, comprising preparing an oral dosage form as disclosed herein. For example, the method can comprise preparing a dosage form comprising an opioid antagonist in non-releasable form such that said dosage form provides a desired analgesic effect and said antagonist does not substantially block the analgesic effect of the opioid agonist when said dosage form is administered orally intact. In alternative embodiments, the effect of the opioid agonist is at least partially blocked when said dosage form tampered with, e.g., chewed, crushed or dissolved in a solvent, and administered orally, intranasally, parenterally or sublingually.

The invention is also directed to a method of treating pain with the dosage forms disclosed herein.

The invention is also directed to methods of preparing the dosage forms disclosed herein. In certain embodiments, the invention comprises a method of preparing an oral dosage form comprising pretreating an opioid antagonist to render it non-releasable; and combining the pretreated antagonist with a releasable form of an opioid agonist and an opioid antagonist in a manner that maintains the integrity of the non-releasable form of the antagonist.

Certain embodiments of the invention are directed to formulations wherein the agonist, releasable antagonist and non-releasable antagonist are interdispersed and are not isolated from each other in three distinct layers. Certain embodiments have two of the three agents interdispersed with the third in a separate and distinct layer. In other embodiments, at least two or all of the ingredients are partially interdispersed. The present invention contemplates all combinations of the agents interdispersed or partially interdispersed in any combination.

The term "analgesic effectiveness" is defined for purposes of the present invention as a satisfactory reduction in or elimination of pain, along with a tolerable level of side effects, as determined by the human patient. The phrase "not substantially blocking the analgesic effect of an opioid agonist" means that the opioid antagonist does not block the effects of the opioid agonist in sufficient degree as to render the dosage form therapeutically less effective for providing analgesia.

The term "an opioid antagonist in a substantially non-releasable form" refers to an opioid antagonist that is not released or substantially not released at one hour after the intact dosage form containing both opioid agonist and the opioid antagonist is orally administered (i.e., without having been tampered with). For purposes of the invention, the amount released after oral administration of the intact dosage form may be measured in-vitro via the dissolution at 1 hour of the dosage form in 900 ml of Simulated Gastric Fluid using a USP Type II (paddle) apparatus at 75 rpm at 37 degrees C. Such a dosage form is also referred to as comprising a "sequestered antagonist".

Although the preferred embodiments of the invention comprise an opioid antagonist in a form that completely prevents the release of the opioid antagonist, the invention also includes an antagonist in a substantially non-releasable form. The term "substantially not released" refers to the antagonist that might be released in a small amount, as long as the amount released does not affect or does not significantly affect analgesic efficacy when the dosage form is orally administered to humans as intended.

In certain preferred embodiments of the invention, the substantially non-releasable form of the antagonist is resistant to laxatives (e.g., mineral oil) used to manage delayed colonic transit and to achlorhydric states.

In certain embodiments, the substantially non-releasable form or non-releasable form of an opioid antagonist comprises an opioid antagonist that is formulated with one or more of pharmaceutically acceptable hydrophobic materials, such that the antagonist is not released or substantially not released during its transit through the gastrointestinal tract when administered orally as intended, without having been tampered with.

In certain embodiments of the present invention, the substantially non-releasable form or non-releasable form of the opioid antagonist is vulnerable to mechanical, thermal and/or chemical tampering, e.g., tampering by means of crushing, shearing, grinding, chewing and/or dissolution in a solvent in combination with heating (e.g., greater than about 45° C.) of the oral dosage form. When thus tampered with, the integrity of the substantially non-releasable form or non-releasable form of the opioid antagonist will be compromised, and the opioid antagonist will be made available to be released. In certain embodiments, when the dosage form is chewed, crushed or dissolved and heated in a solvent, and administered orally, intranasally, parenterally or sublingually, the analgesic or euphoric effect of the opioid is reduced or eliminated. In certain embodiments, the effect of the opioid agonist is at least partially blocked by the opioid antagonist. In certain other embodiments, the effect of the opioid agonist is substantially blocked by the opioid antagonist.

In certain embodiments, the quantity of antagonist released from the dosage form is in a ratio to the agonist which is aversive in physically dependent human subjects when the dosage form is administered at the same amount or at a higher amount than the therapeutically effective amount.

In certain embodiments, the quantity of the antagonist released from the first component is in an amount sufficient to be aversive in physically dependent human subjects when the dosage form is administered at the same amount or at a higher amount than the therapeutically effective amount.

In certain embodiments, the quantity of the antagonist released from the first component is less than the amount sufficient to be aversive in physically dependent human subjects when the dosage form is administered at the same amount or at a higher amount than the therapeutically effective amount.

In certain embodiments, the amount of the antagonist released from the second component is in an amount sufficient to be aversive in physically dependent human subjects when the dosage form is administered at the same amount or at a higher amount than the therapeutically effective amount.

In certain embodiments, the amount of the antagonist released from the second component is less than the amount sufficient to be aversive in physically dependent human subjects when the dosage form is administered at the same amount or at a higher amount than the therapeutically effective amount.

In certain embodiments, the invention comprises a sustained release excipient which provides a sustained release of the opioid agonist.

In certain embodiments, the invention comprises a sustained release excipient which provides a sustained release of the releasable opioid antagonist.

In certain embodiments, the invention comprises a sustained release excipient which provides a sustained release of the opioid agonist and the opioid antagonist.

In certain embodiments, the sequestered antagonist is in the form of multiparticulates individually coated with a material that prevents release of the sequestered antagonist.

In certain embodiments, the sequestered antagonist is in the form of multiparticulates individually coated with a material that substantially prevents release of the sequestered antagonist.

In certain embodiments, the sequestered antagonist is dispersed in a matrix comprising a sequestering material that prevents the release of the sequestered antagonist.

In certain embodiments, the sequestered antagonist is dispersed in a matrix comprising a sequestering material that substantially prevents the release of the sequestered antagonist.

In certain embodiments, the releasable opioid antagonist is the same as the sequestered antagonist.

In certain embodiments, the releasable opioid antagonist is different than the sequestered antagonist.

In certain embodiments, the antagonist is selected from the group consisting of naltrexone, naloxone, nalmephene, cyclazocine, levallorphan, pharmaceutically acceptable salts thereof and mixtures thereof.

In certain embodiments, the releasable antagonist is selected from the group consisting of naltrexone, naloxone, nalmephene, cyclazocine, levallorphan, pharmaceutically acceptable salts thereof and mixtures thereof and the sequestered antagonist is selected from the group consisting of naltrexone, naloxone, nalmephene, cyclazocine, levallorphan, pharmaceutically acceptable salts thereof and mixtures thereof.

In certain embodiments, the opioid is selected from the group consisting of morphine, hydromorphone, hydrocodone, oxycodone, codeine, levorphanol, meperidine, methadone, pharmaceutically acceptable salts thereof and mixtures thereof.

In certain embodiments, the releasable antagonist is an antagonist with minimal oral activity such as naloxone in releasable or "non-sequestered" form and the sequestered antagonist is an orally bioavailable antagonist such as naltrexone. Such a dosage form would be a deterrent to parenteral, nasal and oral abuse of the dosage form upon administration of a tampered dosage form. The inclusion of the releasable non-orally bioavailable antagonist with the opioid agonist would make the formulation more resistant to abuse by making the formulation resistant to parenteral abuse even if the sequestered antagonist was separated from the dosage form, while not affecting the agonist if administered intact.

In certain embodiments, the dosage form has a ratio of releasable opioid antagonist to opioid agonist that is analgesically effective when the combination is administered orally, but which is aversive in physically dependent human subjects when administered at the same amount or at a higher amount than the therapeutically effective amount.

In certain embodiments, the ratio of releasable opioid antagonist to opioid agonist maintains an analgesic effect but does not increase analgesic efficacy of the opioid agonist relative to the same therapeutic amount of opioid analgesic when administered to human patients without the opioid antagonist.

In certain embodiments, the opioid agonist is oxycodone and the releasable antagonist is naltrexone.

In certain embodiments, the ratio of releasable naltrexone to hydrocodone is from about 0.03:1 to about 0.27:1.

In certain embodiments, the ratio of releasable naltrexone to hydrocodone is from about 0.05:1 to about 0.20:1.

In certain embodiments, the releasable opioid antagonist is naltrexone and the opioid agonist is oxycodone, wherein the ratio of releasable naltrexone to oxycodone is from about 0.037:1 to about 0.296:1.

In certain embodiments, the releasable opioid antagonist is naltrexone and the releasable opioid agonist is codeine, wherein the ratio of releasable naltrexone to codeine is from about 0.005:1 to about 0.044:1.

In certain embodiments, the releasable opioid antagonist is naltrexone and the opioid agonist is hydromorphone, wherein the ratio of releasable naltrexone to hydromorphone is from about 0.148:1 to about 1.185:1.

In certain embodiments, the releasable opioid antagonist is naltrexone and the opioid agonist is levorphanol, wherein the ratio of releasable naltrexone to levorphanol is from about 0.278:1 to about 2.222:1.

In certain embodiments, the releasable opioid antagonist is naltrexone and the opioid agonist is meperidine, wherein the ratio of releasable naltrexone to meperidine is from about 0.0037:1 to about 0.0296:1.

In certain embodiments, the releasable opioid antagonist is naltrexone and the opioid agonist is methadone, wherein the ratio of releasable naltrexone to methadone is from about 0.056:1 to about 0.444:1.

In certain embodiments, the releasable opioid antagonist is naltrexone and the opioid agonist is morphine, wherein the ratio of releasable naltrexone to morphine is from about 0.018:1 to about 0.148:1.

In certain embodiments, the releasable opioid antagonist is naltrexone and the opioid agonist is oxycodone, wherein the ratio of releasable naltrexone to oxycodone is from about 0.056:1 to about 0.222:1.

In certain embodiments, the releasable opioid antagonist is naltrexone and the opioid agonist is codeine, wherein the ratio of releasable naltrexone to codeine is from about 0.0083:1 to about 0.033:1.

In certain embodiments, the releasable opioid antagonist is naltrexone and the opioid agonist is hydromorphone, wherein the ratio of releasable naltrexone to hydromorphone is from about 0.222:1 to about 0.889:1.

In certain embodiments, the releasable opioid antagonist is naltrexone and the opioid agonist is levorphanol, wherein the ratio of releasable naltrexone to levorphanol is from about 0.417:1 to about 1.667:1.

In certain embodiments, the releasable opioid antagonist is naltrexone and the opioid agonist is meperidine, wherein the ratio of releasable naltrexone to meperidine is from about 0.0056:1 to about 0.022:1.

In certain embodiments, the releasable opioid antagonist is naltrexone and the opioid agonist is methadone, wherein the ratio of releasable naltrexone to methadone is from about 0.083:1 to about 0.333:1.

In certain embodiments, the releasable opioid antagonist is naltrexone and the opioid agonist is morphine, wherein the ratio of releasable naltrexone to morphine is from about 0.028:1 to about 0.111:1.

In certain embodiments, the releasable antagonist is in an amount to attenuate a side effect of the opioid agonist selected from the group consisting of anti-analgesia, hyperalgesia, hyperexcitability, physical dependence, tolerance, and a combination of any of the foregoing.

In certain embodiments, the amount of antagonist released during the dosing interval enhances the analgesic potency of the opioid agonist.

In certain embodiments, the amount of the releasable opioid receptor antagonist is about 100 to about 1000 fold less than the amount of the opioid agonist.

In certain embodiments, the ratio of the amount of antagonist released from the dosage form after tampering to the amount of the antagonist released from the intact dosage form is about 3, 4, 10, 50 or 100:1; (w:w) or greater, based on the in-vitro dissolution at 1, 8, 24 and/or 36 hours of the dosage form in 900 ml of Simulated Gastric Fluid using a USP Type II (paddle) apparatus at 75 rpm at 37 degrees C., with or without a switch to Simulated Intestinal Fluid after 1 hour.

The term "tampering" means any manipulation by mechanical, thermal and/or chemical means which changes the physical properties of the dosage form, e.g., to liberate the opioid agonist for immediate release if it is in sustained release form, or to make the opioid agonist available for inappropriate use such as administration by an alternate route, e.g., parenterally. The tampering can be, e.g., by means of crushing, shearing, grinding, chewing, dissolution in a solvent, heating (e.g., greater than about 45° C.), or any combination thereof.

The term "at least partially blocking the opioid effect," is defined for purposes of the present invention to mean that the opioid antagonist at least significantly blocks the euphoric effect of the opioid agonist, thereby reducing the potential for abuse of the opioid agonist in the dosage form.

In certain preferred embodiments of the present invention, the substantially non-releasable form or non-releasable form of the opioid antagonist comprises opioid antagonist particles in a coating that substantially prevents or prevents the release of the antagonist. In preferred embodiments, the coating comprising one or more of pharmaceutically acceptable hydrophobic material. The coating is preferably impermeable to the opioid antagonist contained therein and is insoluble in the gastrointestinal system, thus substantially preventing the release of the opioid antagonist when the dosage form is administered orally as intended.

Accordingly, when the oral dosage form is not tampered with as to compromise the integrity of the coating, the opioid antagonist contained therein will not be substantially released during its first hour of transit through the gastrointestinal system, and thus would not be available for absorption. In certain preferred embodiments of the present invention, the hydrophobic material comprises a cellulose polymer or an acrylic polymer that is insoluble in the gastrointestinal fluids and impermeable to the opioid antagonist.

The term "particles" of opioid antagonist, as used herein, refers to granules, spheroids, beads or pellets comprising the opioid antagonist. In certain preferred embodiments, the opioid antagonist particles are about 0.2 to about 2 mm in diameter, more preferably about 0.5 to about 2 mm in diameter.

In certain embodiments of the present invention, the releasable antagonist and the non-releasable antagonist can be contained in the same component. For example, when the opioid antagonist is coated with a coating that substantially prevents its release, and is then mixed with an opioid agonist and compressed into tablets, certain amounts of the coating might be cracked, thus exposing the opioid antagonist to be released upon oral administration. This release can be modified and controlled to provide a desired effect as disclosed herein.

Preferably, the opioid agonist useful for the present invention may be selected from the group consisting of morphine, hydromorphone, hydrocodone, oxycodone, codeine, levorphanol, meperidine, methadone and mixtures thereof. Preferred examples of the opioid antagonist useful for the present invention includes naltrexone, naloxone, nalmefene, cyclazacine, levallorphan, pharmaceutically acceptable salts thereof and mixtures thereof.

In certain embodiments of the present invention, the ratio of the opioid agonist and the opioid antagonist, present in the entire formulation (including releasable and non-releasable form) is about 1:1 to about 50:1 by weight, preferably about 1:1 to about 20:1 by weight or 15:1 to about 30:1. The weight ratio of the opioid agonist to opioid antagonist, as used in this application, refers to the weight of the active ingredients. Thus, for example, the weight of the opioid antagonist excludes the weight of the coating or matrix that renders the opioid antagonist substantially non-releasable, or other possible excipients associated with the antagonist particles. In certain preferred embodiments, the ratio is about 1:1 to about 10:1 by weight. Since a portion of the opioid antagonist is in a non-releasable from, the amount of such antagonist within the dosage form may be varied more widely than the opioid agonist/antagonist combination dosage forms where both are available for release upon administration as the formulation does not depend on differential metabolism or hepatic clearance for proper functioning. For safety reasons, the amount of the opioid antagonist present in the entire dosage form is selected as not to be harmful to humans even if fully released by tampering with the dosage form.

In certain preferred embodiments of the present invention, the opioid agonist comprises hydrocodone, oxycodone or pharmaceutically acceptable salts thereof and the opioid antagonist, present in a substantially non-releasable form, comprises naloxone, naltrexone or pharmaceutically acceptable salts thereof.

The oral dosage form containing an opioid agonist in combination with the releasable and non-releasable opioid antagonist includes, but are not limited to, tablets or capsules. The dosage forms of the present invention may include any desired pharmaceutical excipients known to those skilled in the art. The oral dosage forms may further provide an immediate release of the opioid agonist. In certain embodiments, the oral dosage forms of the present invention provide a sustained release of the opioid agonist contained therein, or a combination of controlled and immediate release agonist. Such dosage forms of the opioid agonist may be prepared in accordance with formulations/methods of manufacture known to those skilled in the art of pharmaceutical formulation.

The benefits of the abuse-resistant dosage form are especially great in connection with oral dosage forms of strong opioid agonists (e.g., oxycodone or hydrocodone), which provide valuable analgesics but can be the subject of abuse. This is particularly true for sustained release opioid agonist products which have a large dose of a desirable opioid agonist intended to be released over a period of time in each dosage unit. Drug abusers take such sustained-release product and crush, grind, extract or otherwise damage the product so that the full contents of the dosage form become available for immediate absorption. Since such tampering of the dosage form of the invention results in opioid antagonist (in addition to the releasable antagonist) also becoming available for absorption, the present invention provides a means for frustrating such abuse. In addition, the present invention addresses the risk of overdose to ordinary patients from "dumping" effect of the full dose of the opioid agonist if the product is accidentally chewed or crushed.

The term "sustained release" is defined for purposes of the present invention as the release of the opioid agonist from the oral dosage form at such a rate that blood (e.g., plasma) concentrations (levels) are maintained within the therapeutic range (above the minimum effective analgesic concentration or "MEAC") but below toxic levels over a period of 8 to 24 hours, preferable over a period of time indicative of a twice-a-day or a once-a-day formulation.

The invention may provide for a safer product (e.g., less respiratory depression), if the product is misused, as well as one with less risk of abuse.

In certain embodiments, a combination of two opioid agonists is included in the formulation. In further embodiments, one or more opioid agonist is included and a further non-opioid drug is also included. Such non-opioid drugs would preferably provide additional analgesia, and include, for example, aspirin, acetaminophen, non-steroidal anti-inflammatory drugs ("NSAIDS"), NMDA antagonists, and cycooxygenase-II inhibitors ("COX-II inhibitors").

In yet further embodiments, a non-opioid drug can be included which provides a desired effect other than analgesia, e.g., antitussive, expectorant, decongestant, or antihistamine drugs, and the like.

For purposes of the present invention, the term "opioid agonist" is interchangeable with the term "opioid" or "opioid analgesic" and shall include combinations of more than one opioid agonist, and also include the base of the opioid, mixed agonist-antagonists, partial agonists, pharmaceutically acceptable salts thereof, stereoisomers thereof, ethers and esters thereof, and mixtures thereof.

For purposes of the present invention, the term "opioid antagonist" shall include combinations of more than one opioid antagonist, and also include the base, pharmaceutically acceptable salts thereof, stereoisomers thereof, ethers and esters thereof, and mixtures thereof.

The invention disclosed herein is meant to encompass all pharmaceutically acceptable salts thereof of the disclosed opioid agonists and antagonists. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

Some of the opioid agonists and antagonists disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The present invention is further directed to a method of decreasing the potential for abuse of an opioid agonist in an oral dosage form. The method comprises providing the opioid agonist in an oral dosage form as described herein.

DETAILED DESCRIPTION OF THE INVENTION

It has been postulated that there exists at least three subspecies of opioid receptors, designated mu, kappa, and delta. Within this framework, the mu receptor is considered to be involved in the production of superspinal analgesia, respiratory depression, euphoria, and physical dependence. The kappa receptor is considered to be involved in inducing spinal analgesia, miosis and sedation. Activation of the gamma receptors causes dysphoria and hallucinations, as well as respiratory and vasomotor stimulatory effects. A receptor distinct from the mu receptor and designated gamma has been described in the mouse vas deferens, Lord, et al. *Nature,* 1977, 267, 495-99. Opioid agonists are thought to exert their agonist actions primarily at the mu receptor and to a lesser degree at the kappa receptor. There are a few drugs that appear to act as partial agonists at one receptor type or another. Such drugs exhibit a ceiling effect. Such drugs include nalorphine, propiram, and buprenorphine. Still other drugs act as competitive antagonists at the mu receptor and block the effects of morphine-like drugs, by exerting their actions at the kappa and omega receptors. The term agonist-antagonist has evolved to describe such mechanism of actions.

The present invention is directed to a controlled release opioid analgesic, similar in analgesic spectrum to existing controlled-release opioid analgesics, which is formulated in order to reduce and minimize misuse, abuse and diversion. In certain embodiments, these characteristics are conferred by the inclusion of an opioid antagonist such as naltrexone HCl, which is itself formulated in a unique controlled release matrix. The properties of this formulation are developed to liberate the antagonist in conditions of misuse or tampering yet a negligible amount of antagonist would be released (an amount which does not affect the analgesia experienced by the patient) under the prescribed conditions of use.

In certain embodiments of the invention, the release for the antagonist component of the formulation is expressed in terms of a ratio of the release achieved after tampering, e.g., by crushing or chewing, relative to the amount released from the intact formulation. The ratio is therefore expressed as [Crushed]/[Whole], and it is desired that this ratio have a numerical range of at least 3:1 or greater (crushed release in 1 hour/intact release in 1 hour).

In certain preferred embodiments, the opioid antagonist in a substantially non-releasable form comprises opioid antagonist particles coated with a coating that substantially prevents its release. In preferred embodiments, such coating surrounds the antagonist particles and is impermeable to the drug and is insoluble in the gastrointestinal system. When the dosage form of the present invention is orally administered to humans, the opioid antagonist is not substantially released from the coating and is, therefore, not available for absorption into the body. Thus, the opioid antagonist, although present in the dosage form, does not substantially block the analgesic effectiveness of the opioid agonist. However, if the oral dosage form of the present invention is tampered with as to compromise the integrity of the coating, the opioid antagonist contained therein would be made available to at least partially block the effect of the opioid agonist. This characteristic decreases the potential for abuse or diversion of the opioid agonist in the oral dosage form. For example, if one attempts to abuse the drug contained in the oral dosage form of the present invention by, e.g., chewing, crushing, grinding or dissolving it in a solvent with heat (e.g., greater than about 45° C. to about 50° C.), the coating will be damaged and will no longer prevent the opioid antagonist from being released. Upon administration, the opioid antagonist will be released and significantly block the euphoric effect of the opioid agonist.

In certain embodiments of the invention, the ratio of the opioid agonist to the coated opioid antagonist is such that when the oral dosage form is tampered with as to compromise the integrity of the coating that renders the opioid antagonist substantially non-releasable, the euphoric effect of the agonist would be negated by the opioid antagonist when misused by a human subject orally, parenterally, intranasally or sublingually. In certain preferred embodiments of the invention, the euphoric effect of the opioid agonist would be negated by the opioid antagonist when misused parenterally or sublingually.

In certain other embodiments of the present invention, the opioid antagonist in a substantially non-releasable form comprises an opioid antagonist dispersed in a matrix that renders the antagonist substantially non-releasable, wherein the matrix comprises one or more of a pharmaceutically acceptable hydrophobic material. The antagonist is substantially not released from the matrix, thus is not made available to be absorbed during its transit through the gastrointestinal system.

In certain other embodiments of the present invention, the opioid antagonist in a matrix that renders the antagonist substantially non-releasable comprises an opioid antagonist dispersed in a melt-extruded matrix, wherein the matrix comprises one or more of a pharmaceutically acceptable hydrophobic material.

All discussion herein directed to the non-releasable component and its release upon tampering as well as all general discussion is in addition to the releasable antagonist of the intact dosage form. As discussed, the releasable form of the antagonist can be released from the same component as the non-releasable, from a separate component or from a combination of both components.

The releasable antagonist of the present invention can comprises an amount of the opioid antagonist such as naltrexone in an amount (i) which does not cause a reduction in the level of analgesia elicited from the dosage form upon oral administration to a non-therapeutic level and (ii) which provides at least a mildly negative, "aversive" experience in physically dependent human subjects, for example, physically dependent addicts (e.g., precipitated abstinence syndrome) when taking one dosage form or more than one dosage form. Preferably, the amount of antagonist included in the intact oral dosage form is (iii) less positively reinforcing (e.g., less "liked") by a non-physically dependent human subject, e.g., opioid addict, than a comparable oral dosage form without the antagonist included.

The amount of antagonist which is useful to achieve parameters (i)-(iii) set forth in the preceding paragraph may be determined at least in part, for example, through the use of "surrogate" tests, such as a VAS scale (where the subject grades his/her perception of the effect of the dosage form) and/or via a measurement such as pupil size (measured by pupillometry). Such measurements allow one skilled in the art to determine the dose of antagonist relative to the dose of agonist which causes a diminution in the opiate effects of the agonist. Subsequently, one skilled in the art can determine the level of opioid antagonist that causes aversive effects in physically dependent subjects as well as the level of opioid antagonist that minimizes "liking scores" or opioid reinforcing properties in non-physically dependent addicts. Once these levels of opioid antagonist are determined, it is then possible to determine the range of antagonist dosages at or below this level which would be useful in achieving parameters (i)-(iii) set forth in the preceding paragraph.

In certain preferred embodiments, the opioid agonist or analgesic is selected from the group consisting of hydrocodone, morphine, hydromorphone, oxycodone, codeine, levorphanol, meperidine, methadone, or salts thereof, or mixtures thereof. In certain preferred embodiments, the opioid agonist is hydrocodone or oxycodone. Equianalgesic doses of these opioids, in comparision to a 15 mg dose of hydrocodone, are set forth in Table 1 below:

TABLE 1

Equianalgesic Doses of Opioids

| Opioid | Calculated Dose (mg) |
|---|---|
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

Based on a ratio of releasable naltrexone in an amount from about 0.5 to about 4 mg per 15 mg of hydrocodone, the approximate ratio of naltrexone to 1 mg of each opioid is set forth in Table 2:

TABLE 2

Weight Ratio of Naltrexone per Dose Opioid

| Opioid | Weight Ratio Naltrexone per 1 mg Opioid |
|---|---|
| Oxycodone | 0.037 to 0.296 |
| Codeine | 0.005 to 0.044 |
| Hydrocodone | 0.033 to 0.267 |
| Hydromorphone | 0.148 to 1.185 |
| Levorphanol | 0.278 to 2.222 |
| Meperidine | 0.0037 to 0.0296 |
| Methadone | 0.056 to 0.444 |
| Morphine | 0.018 to 0.148 |

Based on a ratio of about 0.75 mg to about 3 mg naltrexone per 15 mg hydrocodone of naltrexone, the approximate ratio of naltrexone to 1 mg of each opioid is set forth in Table 3:

TABLE 3

Weight Ratio of Naltrexone per Dose Opioid

| Opioid | Weight Ratio Naltrexone |
|---|---|
| Oxycodone | 0.056 to 0.222 |
| Codeine | 0.0083 to 0.033 |
| Hydrocodone | 0.050 to 0.200 |
| Hydromorphone | 0.222 to 0.889 |
| Levorphanol | 0.417 to 1.667 |
| Meperidine | 0.0056 to 0.022 |
| Methadone | 0.083 to 0.333 |
| Morphine | 0.028 to 0.111 |

Ratios of opioids to other antagonists besides naltrexone can be obtained by comparing equivalent doses of other antagonists to equal doses of naltrexone. The specification and examples of PCT/US98/27257 which discloses releasable opioid antagonist/agonist formulations is hereby incorporated by reference in combination with the sequestered antagonist as disclosed herein.

The releasable antagonist of the present invention can comprises an amount of the opioid antagonist which can selectively enhancing the potency of the opioid agonists and simultaneously attenuating undesirable side-effects, including physical dependence, caused by the chronic administration of said opioid agonists. Morphine and other bimodally-acting (inhibitory/excitatory) opioid agonists bind to and activate inhibitory and excitatory opioid receptors on nociceptive neurons mediating pain. Activation of inhibitory receptors by said agonists causes analgesia. Activation of excitatory receptors by said agonists results in anti-analgesic effects, development of physical dependence, tolerance, hyperexcitability, hyperalgesia and other undesirable side-effects. The co-administration of the releasable opioid antagonist which binds to and inactivates excitatory opioid receptors results in the blocking of excitatory anti-analgesic side-effects of said opioid agonists on these neurons, thereby resulting in enhanced analgesic potency which permits the use of lower doses of morphine or other conventional opioid analgesics. The specification and examples of U.S. Pat. No. 5,472,943 which describes such formulations and methods is hereby incorporated by reference in combination with the sequestered antagonist as disclosed herein.

All known references of releasable opioid antagonists with opioid agonists such as U.S. Pat. No. 3,773,955 (Pachter, et al.); U.S. Pat. No. 3,493,657 (Lewenstein, et al.) U.S. Pat. No. 4,457,933 (Gordon, et al.); U.S. Pat. No. 4,582,835 (Lewis) U.S. Pat. Nos. 5,512,578; 5,472,943; 5,580,876; and U.S. Pat. No. 5,767,125 (Crain) and U.S. Pat. Nos. 4,769,372 and 4,785,000 (Kreek) can be combined with a sequestered antagonist as disclosed herein and all of these references are hereby incorporated by reference.

U.S. Provisional Application Nos. 60/181,369 and 60/181,358 both filed Feb. 6, 2000 are hereby incorporated by reference in combination with the three component invention as disclosed herein.

All commercial products of opioid agonist and releasable antagonists can be combined with a sequestered antagonist as disclosed herein. For example, Talwin NX can be formulated with a sequestered antagonist to reduce oral abuse as well as parenteral abuse of the opioid therein.

In preferred embodiments, opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, prophetazine, promedol, properidine, propoxyphene, sufentanil, tilidine, tramadol, mixtures of any of the foregoing, salts of any of the foregoing, and the like. In certain embodiments, the amount of the opioid agonist in the claimed opioid composition may be about 75 ng to 750 mg.

Although hydrocodone and oxycodone are effective in the management of pain, there has been an increase in their abuse by individuals who are psychologically dependent on opioids or who misuse opioids for non-therapeutic reasons. Previous experience with other opioids has demonstrated a decreased abuse potential when opioids are administered in combination with a narcotic antagonist especially in patients who are ex-addicts. Weinhold L L, et al. Buprenorphine Alone and in Combination with Naltrexone in Non-Dependent Humans, *Drug and Alcohol Dependence* 1992; 30:263-274; Mendelson J., et al., Buprenorphine and Naloxone Interactions in Opiate-Dependent Volunteers, *Clin Pharm Ther.* 1996; 60:105-114; both of which are hereby incorporated by reference. These combinations, however, do not contain the opioid antagonist that is in a substantially non-releasable form. Rather, the opioid antagonist is released in the gastrointestinal system when orally administered and is made available for absorption, relying on the physiology of the host to differentially metabolize the agonist and antagonist and negate the agonist effects.

Hydrocodone is a semisynthetic narcotic analgesic and antitussive with multiple central nervous system and gastrointestinal actions. Chemically, hydrocodone is 4,5-epoxy-3-methoxy-17-methylmorphinan-6-one, and is also known as dihydrocodeinone. Like other opioids, hydrocodone may be habit forming and may produce drug dependence of the morphine type. In excess doses hydrocodone, like other opium derivatives, will depress respiration.

Oral hydrocodone is also available in Europe (Belgium, Germany, Greece, Italy, Luxembourg, Norway and Switzerland) as an antitussive agent. A parenteral formulation is also available in Germany as an antitussive agent. For use as an analgesic, hydrocodone bitartrate is commercially available in the United States only as a fixed combination with non-opiate drugs (i.e., ibuprofen, acetaminophen, aspirin, etc.) for relief of moderate or moderately severe pain.

A common dosage form of hydrocodone is in combination with acetaminophen, and is commercially available, e.g., as Lortab® in the U.S. from UCB Pharma, Inc. as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen; and 7.5 mg hydrocodone bitartrate and 750 mg acetaminophen. Hydrocodone in combination with aspirin is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. A relatively new formulation comprises hydrocodone bitartrate and ibuprofen. Vicoprofen®, commercially available in the U.S. from Knoll Laboratories, is a tablet containing 7.5 mg hydrocodone bitartrate and 200 mg ibuprofen. The present invention is contemplated to encompass all such formulations, with the inclusion of an opioid antagonist in releasable and non-releasable form.

Oxycodone, chemically known as 4,5-expoxy-14-hydroxy-3-methoxy-17-methylmorphinan-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug.

Oxycodone is commercially available in the United States, e.g., as Oxycontin® from Purdue Pharma L.P. as controlled-release tablets for oral administration containing 10 mg, 20 mg, 40 mg or 80 mg oxycodone hydrochloride, and as OxyIR™, also from Purdue Pharma L.P., as immediate-release capsules containing 5 mg oxycodone hydrochloride. The present invention is contemplated to encompass all such formulations, with the inclusion of an opioid antagonist in a substantially non-releasable form.

In preferred embodiments, the opioid antagonist of the present invention includes naltrexone, nalmefene, cyclazacine, levallorphan and mixtures thereof. In certain preferred embodiments, the opioid antagonist is naloxone or naltrexone. In certain embodiments, the amount of the opioid antagonist, present in a substantially non-releasable form, may be about 10 ng to 275 mg.

Naloxone is an opioid antagonist which is almost void of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously in man prevent or promptly reverse the effects of morphine-like opioid agonist. One mg of naloxone intravenously has been reported to completely block the effect of 25 mg of heroin. The effects of naloxone are seen almost immediately after intravenous administration. The drug is absorbed after oral administration, but has been reported to be metabolized into an inactive form rapidly in its first passage through the liver such that it has been reported to have significantly lower potency than as when parenterally administered. Oral dosage of more than 1 g have been reported to be almost completely metabolized in less than 24 hours. It has been reported that 25% of naloxone administered sublingually is absorbed. Weinberg, et al., Sublingual Absorption of selected Opioid Analgesics, *Clin Pharmacol Ther.* (1988); 44:335-340.

Other opioid antagonists, for example, cyclazocine and naltrexone, both of which have cyclopropylmethyl substitutions on the nitrogen, retain much of their efficacy by the oral route and their durations of action are much longer, approaching 24 hours after oral doses.

In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located on the nitrogen atom of oxymorphone with a cyclopropylmethyl group. The hydrochloride salt of naltrexone is soluble in water up to about 100 mg/cc. The pharmacological and pharmacokinetic properties of naltrexone have been evaluated in multiple animal and clinical studies. See, e.g., Gonzalez J P, et al. Naltrexone: A review of its Pharmacodynamic and Pharmacokinetic Properties and Therapeutic Efficacy in the Management of Opioid Dependence. *Drugs* 1988; 35:192-213, hereby incorporated by reference. Following oral administration, naltrexone is rapidly absorbed (within 1 hour) and has an oral bioavailability ranging from 5-40%. Naltrexone's protein binding is approximately 21% and the volume of distribution following single-dose administration is 16.1 L/kg.

Naltrexone is commercially available in tablet form (Revia®, DuPont) for the treatment of alcohol dependence and for the blockade of exogenously administered opioids. See, e.g., Revia (naltrexone hydrochloride tablets). *Physician's Desk Reference* 51$^{st}$ ed., Montvale, N.J. "Medical Economics" 1997; 51:957-959. A dosage of 50 mg Revia® blocks the pharmacological effects of 25 mg IV administered heroin for up to 24 hours.

It is known that when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with narcotic addicts having good prognosis, as part of a comprehensive occupational or rehabilitative program involving behavioral control or other compliance enhancing methods. For treatment of narcotic dependence with naltrexone, it is desirable that the patient be opioid-free for at least 7-10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone has also been used for the treatment of alcoholism as an adjunct with social and psychotherapeutic methods.

In certain embodiments of the present invention, ratio of the opioid agonist to the substantially non-releasable form of an opioid antagonist in the oral dosage form is such that the effect of the opioid agonist is at least partially blocked when the dosage form is chewed, crushed or dissolved in a solvent and heated, and administered orally, intranasally, parenterally or sublingually. Since the oral dosage form of the present invention, when administered properly as intended, would not substantially release the opioid antagonist, the amount of such antagonist may be varied more widely than if the opioid antagonist is available to be released into the gastrointestinal system upon oral administration. For safety reasons, the amount of the antagonist present in a substantially non-releasable form should not be harmful to humans even if fully released. The ratio of particular opioid agonist to antagonist can be determined without undue experimentation by one skilled in the art.

The oral dosage form of the present invention may further include, in addition to an opioid agonist and releasable and non-releasable antagonist, one or more drugs that may or may not act synergistically therewith. Thus, in certain embodiments, a combination of two opioid agonists may be included in the dosage form, in addition to the opioid antagonist. For example, the dosage form may include two opioid agonists having different properties, such as half-life, solubility, potency, and a combination of any of the foregoing. In yet further embodiments, one or more opioid agonist is included and a further non-opioid drug is also included, in addition to the opioid antagonist. Such non-opioid drugs would preferably provide additional analgesia, and include, for example, aspirin, acetaminophen; non-steroidal anti-inflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cyclooxygenase-II inhibitors ("COX-II inhibitors"); and/or glycine receptor antagonists.

In certain preferred embodiments of the present invention, the invention allows for the use of lower doses of the opioid analgesic by virtue of the inclusion of an additional non-opioid agonist, such as an NSAID or a COX-2 inhibitor. By using lower amounts of either or both drugs, the side effects associated with effective pain management in humans are reduced.

Suitable non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$ a phenothiazine such as trifluoperazine or a naphthalenesulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al.), all of which are hereby incorporated by reference. The NMDA antagonist may be included alone, or in combination with a local anesthetic such as lidocaine, as described in these Mayer, et. al. patents.

The treatment of chronic pain via the use of glycine receptor antagonists and the identification of such drugs is described in U.S. Pat. No. 5,514,680 (Weber, et al.), hereby incorporated by reference.

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,474,995; 5,639,780; 5,604,253; 5,552,422; 5,510,368; 5,436,265; 5,409,944; and 5,130,311, all of which are hereby incorporated by reference. Certain preferred COX-2 inhibitors include celecoxib (SC-58635), DUP-697, flosulide (CGP-28238), meloxicam, 6-methoxy-2 naphthylacetic acid (6-MNA), MK-966 (also known as Vioxx), nabumetone (prodrug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic.

In yet further embodiments, a non-opioid drug can be included which provides a desired effect other than analgesia, e.g., antitussive, expectorant, decongestant, antihistamine drugs, local anesthetics, and the like.

Preparation of Opioid Antagonist in a Substantially Non-Releasable or Non-Releasable Form In certain embodiments of the present invention, an opioid antagonist in a substantially non-releasable form may be prepared by combining the antagonist with one or more of a pharmaceutically acceptable hydrophobic material. For example, opioid antagonist particles may be coated with coating that substantially prevents the release of the antagonist, the coating comprising the hydrophobic materials(s). Another example would be an opioid antagonist that is dispersed in a matrix that renders the antagonist to be substantially non-releasable, the matrix comprising the hydrophobic materials(s). In certain embodiments, the pharmaceutical acceptable hydrophobic material comprises a cellulose polymer selected from the group consisting of ethylcellulose, cellulose acetate, cellulose propionate (lower, medium or higher molecular weight), cellulose acetate propionate, cellulose acetate butyrate, cellulose acetate phthalate and cellulose triacetate. An example of ethylcellulose is one that has an ethoxy content of 44 to 55%. Ethylcellulose may be used in the form of an alcoholic solution. In certain other embodiments, the hydrophobic material comprises polylactic acid, polyglycolic acid or a co-polymer of the polylactic and polyglycolic acid.

In certain embodiments, the hydrophobic material may comprise a cellulose polymer selected from the group consisting of cellulose ether, cellulose ester, cellulose ester ether, and cellulose. The cellulosic polymers have a degree of substitution, D.S., on the anhydroglucose unit, from greater than zero and up to 3 inclusive. By degree of substitution is meant the average number of hydroxyl groups present on the anhydroglucose unit comprising the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, mono, di, and tricellulose alkanylates, moni, di, and tricellulose aroylates, and mono, di, and tricellulose alkenylates. Exemplary polymers include cellulose acetate having a D.S. and an acetyl content up to 21%; cellulose acetate having an acetyl content up to 32 to 39.8%; cellulose acetate having a D.S. of 1 to 2 and an acetyl content of 21 to 35%; cellulose acetate having a D.S. of 2 to 3 and an acetyl content of 35 to 44.8%.

More specific cellulosic polymers include cellulose propionate having a D.S. of 1.8 and a propyl content of 39.2 to 45 and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylate having a D.S. of 2.9 to 3 such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate and cellulose acetate propionate.

Additional cellulose polymers useful for preparing an opioid antagonist in a substantially non-releasable form includes acetaldehyde dimethyl cellulose acetate, cellulose acetate ethylcarbamate, cellulose acetate methylcarbamate, and cellulose acetate dimethylaminocellulose acetate.

An acrylic polymer useful for preparation of the opioid antagonist in a substantially non-releasable form includes, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Rohm Pharma GmbH and sold under the Eudragit® RS trademark. Eudragit RS30D is preferred. Eudragit® RS is a water insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins such as Eudragit® RS may be used in the form of an aqueous suspension.

In certain embodiments of the invention, the acrylic polymer may be selected from the group consisting of acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

When the opioid antagonist in a substantially non-releasable form comprises opioid antagonist particles coated with a coating that renders the antagonist substantially non-releasable, and when a cellulose polymer or an acrylic polymer is used for preparation of the coating composition, suitable plasticizers, e.g., acetyl triethyl citrate and/or acetyl tributyl citrate may also be admixed with the polymer. The coating may also contain additives such as coloring agents, talc and/or magnesium stearate, which are well known in the coating art.

The coating composition may be applied onto the opioid antagonist particles by spraying it onto the particles using any suitable spray equipment known in the part. For example, a Wuster fluidized-bed system may be used in which an air jet, injected from underneath, fluidizes the coated material and effects drying while the insoluble polymer coating is sprayed on. The thickness of the coating will depend on the characteristics of the particular coating composition being used. However, it is well within the ability of one skilled in the art to determine by routine experimentation the optimum thickness of a particular coating required for a particular dosage form of the present invention.

The pharmaceutically acceptable hydrophobic material useful for preparing an opioid antagonist in a substantially non-releasable form includes a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesthers, polydioxanone, polygluconate, polylactic-acid-polyethylene oxide copolymers, poly(hydroxybutyrate), polyphosphoesther or mixtures or blends of any of these.

In certain embodiments, biodegradable polymer comprises a poly(lactic/glycolic acid), a copolymer of lactic and glycolic acid, having molecular weight of about 2,000 to about 500,000 daltons. The ratio of lactic acid to glycolic acid is from about 100:0 to about 25:75, with the ratio of lactic acid to glycolic acid of 65:35 being preferred.

Poly(lactic/glycolic acid) may be prepared by the procedure set forth in U.S. Pat. No. 4,293,539 (Ludwig et al.), the disclosure of which is hereby incorporated by reference in its entirety. In brief, Ludwig prepares the copolymer by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100 C to about 250 C for about 48 to about 96 hours, preferably under a reduced pressure to facilitate removal of water and by-products. Poly(lactic/glycolic acid) is then recovered by filtering the molten reaction mixture in an organic solvent such as dichloromethane or acetone and then filtering to remove the catalyst.

Once the opioid antagonist in a substantially non-releasable form is prepared, it may be combined with an opioid agonist and releasable antagonist, along with conventional excipients known in the art, to prepare the oral dosage form of the present invention.

In certain preferred embodiments of the invention, the oral dosage form is a capsule or a tablet. When being formulated as a tablet, the agents may be combined with one or more inert, non-toxic pharmaceutical excipients which are suitable for the manufacture of tablets. Such excipients include, for example, an inert diluent such as lactose; granulating and disintegrating agents such as cornstarch; binding agents such as starch; and lubricating agents such as magnesium stearate.

The oral dosage form of the present invention may be formulated to provide immediate release of the opioid agonist contained therein. In other embodiments of the invention, however, the oral dosage form provides sustained-release of the opioid agonist.

In certain embodiments, the oral dosage forms providing sustained release of the opioid agonist and/or releasable antagonist may be prepared by admixing the opioid antagonist in a substantially non-releasable form with the agonist and releasable antagonist and desirable pharmaceutical excipients to provide a tablet, and then coating the tablet with a sustained-release tablet coating.

In certain embodiments of the invention, sustained release opioid agonist tablets may be prepared by admixing the substantially non-releasable form of an opioid antagonist with a releasable opioid antagonist and agonist in a matrix that provides the tablets with sustained-releasing properties.

Detailed description for preparing sustained-release oral dosage forms according to the present invention is set forth below.

Preparation of Controlled Release Dosage Forms Containing an Opioid Agonist and a Substantially Non-Releasable Form of an Opioid Antagonist A combination of the opioid agonist and a substantially non-releasable form of an opioid antagonist may be formulated as a controlled or sustained release oral formulation in any suitable tablet, coated tablet or multiparticulate formulation known to those skilled in the art. The sustained release dosage form may optionally include a sustained release carrier which is incorporated into a matrix along with the opioid agonist and a non-available form of an opioid antagonist, or may be applied as a sustained release coating.

In embodiments in which the opioid agonist comprises hydrocodone, the sustained release oral dosage forms may include analgesic doses from about 8 mg to about 50 mg of hydrocodone per dosage unit. In sustained release oral dosage forms where hydromorphone is the therapeutically active opioid, it is included in an amount from about 2 mg to about 64 mg hydromorphone hydrochloride. In another embodiment, the opioid agonist comprises morphine, and the sustained release oral dosage forms of the present invention include from about 2.5 mg to about 800 mg morphine, by weight. In yet another embodiment, the opioid agonist comprises oxycodone and the sustained release oral dosage forms include from about 2.5 mg to about 800 mg oxycodone. In certain preferred embodiments, the sustained release oral dosage forms include from about 20 mg to about 30 mg oxycodone. Controlled release oxycodone formulations are known in the art. The following documents describe various controlled release oxycodone formulations suitable for use in the invention described herein, and processes for their manufacture: U.S. Pat. Nos. 5,266,331; 5,549,912; 5,508,042; and 5,656,295. The opioid agonist may comprise tramadol and the sustained release oral dosage forms may include from about 25 mg to 800 mg tramadol per dosage unit. The dosage form may contain more than one opioid agonist to provide a substantially equivalent therapeutic effect. Alternatively, the dosage form may contain molar equivalent amounts of other salts of the opioid agonists useful in the present invention.

In one preferred embodiment of the present invention, the sustained release dosage form comprises such particles comprising the opioid agonist, wherein the particles have diameter from about 0.1 mm to about 2.5 mm, preferably from about 0.5 mm to about 2 mm.

The opioid agonist particles are preferably film coated with a material that permits release of the opioid agonist at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, nonYtoxic, inert, and tack-free.

The dosage forms comprising an opioid agonist and a substantially non-releasable opioid antagonist may optionally be coated with one or more materials suitable for the regulation of the opioid agonist release or for the protection of the formulation. In one embodiment, coatings are provided to permit either pH-dependent or pH-independent release, e.g., when exposed to gastrointestinal fluid. A pH-dependent coating serves to release the opioid in desired areas of the gastro-intestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release of the opioid regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the opioid analgesic (with or without the COX-2 inhibitor) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493, assigned to the Assignee of the present invention and hereby incorporated by reference.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When a hydrophobic controlled release coating material is used to coat inert pharmaceutical beads such as nu pariel 18/20 beads, which are already coated with an opioid agonist, a plurality of the resultant solid controlled release beads may thereafter be placed in a gelatin capsule, with the opioid antagonist in a substantially non-releasable form. The dosage form provides an effective controlled release dose of the opioid agonist when ingested and contacted by an environmental fluid, e.g., gastric fluid or dissolution media.

The controlled release bead formulations of the present invention slowly release the opioid agonist, e.g., when ingested and exposed to gastric fluids, and then to intestinal fluids. The controlled release profile of the formulations of the invention can be altered, for example, by varying the amount of overcoating with the hydrophobic material, altering the manner in which the plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with an opioid agonist may be prepared, e.g., by dissolving the drug in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Preformulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the therapeutically active agent by spraying using any suitable spray equipment known in the art. In a preferred method, a Wurster fluidizedBbed system is used in which an air jet, injected from underneath, fluidizes the core material and effects drying while the acrylic polymer coating is sprayed on. A sufficient amount of the hydrophobic material to obtain a predetermined controlled release of said therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

Matrix Formulations

In other embodiments of the present invention, the controlled release formulation is achieved via a matrix having a controlled release coating as set forth above. The present invention also comprises sustained-release tablets comprising an opioid agonist and opioid antagonist particles coated with a coating that renders the antagonist substantially non-releasable, wherein the agonist and the antagonist are dispersed in a controlled release matrix that affords in-vitro dissolution rates of the opioid agonist within the preferred ranges and that releases the opioid agonist in a pH-dependent or pH-independent manner. The materials suitable for inclusion in a controlled release matrix will depend on the method used to form the matrix.

For example, a matrix in addition to the opioid agonist and the substantially non-releasable form of the coated opioid antagonist, may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the opioid may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30° to about 200° C., preferably from about 45° to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

Processes for Preparing Matrix—Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opioid or an opioid salt; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and pheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques, as long as the techniques used do not damage the integrity of the substantially non-releasable form of the opioid antagonist added during the preparation of the matrix to the extent that sufficient amount of the opioid antagonist becomes available to be released into the gastrointestinal system upon oral administration. Alternatively, the melt extrusion step may be performed with the opioid agonist to produce sustained release particles of the agonist, which may then be combined with the substantially non-releasable form of the opioid antagonist. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598, assigned to the Assignee of the present invention and hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

Melt Extrusion Multiparticulates

The preparation of a suitable melt-extruded matrix according to the present invention may, for example, include the steps of blending the opioid analgesic, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then blended with the opioid antagonist particles coated with a coating that renders the antagonist substantially non-releasable and divided into unit doses. The extrudate preferably has a diameter of from about 0.1 to about 5 mm and provides sustained release of the opioid agonist for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and combining the particles with the coated opioid antagonist particles and dividing them into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is combined with the coated opioid antagonist particles and compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553-1593 (1980), incorporated by reference herein.

In yet another preferred embodiment, the coated opioid antagonist particles are added during the extrusion process and the extrudate can be shaped into tablets as set forth in U.S. Pat. No. 4,957,681 (Klimesch, et al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opioid analgesic compound utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release opioid agonist for prompt therapeutic effect. The immediate release opioid agonist may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the opioid agonist, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the opioid agonist and/or coated opioid antagonist particles, which are added thereafter to the extrudate. Such formulations typically will have the drugs blended together with the extruded matrix material, and then the mixture would be tableted in order to provide a slow release of the opioid agonist. Such formulations may be advantageous, for example, when the therapeutically active agent included in the formulation is sensitive to temperatures needed for softening the hydrophobic material and/or the retardant material.

DETAILED DESCRIPTION OF PREFERRED EMBODIMENTS

The following examples illustrate various aspects of the present invention. They are not to be construed to limit the claims in any manner whatsoever.

Example 1

In Example 1, a substantially non-releasable form of an opioid antagonist (naltrexone HCl) is prepared by coating naltrexone particles with a coating that renders the antagonist substantially non-releasable.

Formula:

| Ingredients | Amt/unit (mg) |
|---|---|
| LOADING | |
| Naltrexone HCl | 5.0 |
| Sugar Spheres (30/35 mesh) | 50.0 |
| Opadry White Y-5-7068 | 2.5 |
| Purified Water | 42.5* |
| OVERCOATING | |
| Opadry White Y-5-7068 | 3.02 |
| Purified Water | 17.11* |
| NON-RELEASE COATING (FOR RENDERING OPIOID ANTAGONIST SUBSTANTIALLY NON-RELEASABLE) | |
| Eudragit RS30D (dry wt.) | 12.10 |
| Triethyl Citrate | 2.42 |
| Talc | 4.84 |
| Purified Water | 49.21* |
| OVERCOATING | |
| Opadry White Y-5-7068 | 4.12 |
| Purified Water | 23.35* |
| Total | 84.0 |

*Remains in product as residual moisture only.

Process:

| 1. Solution Preparation | Dissolve the Naltrexone HCl in Purified Water. Once dissolved, add the Opadry White and continue mixing until a homogeneous dispersion is yielded. |
|---|---|
| 2. Loading | Apply the above dispersion onto the Sugar Spheres using a fluid bed coating machine. |
| 3. Overcoating | Prepare an overcoating solution by dispersing Opadry White in Purified Water. Apply this dispersion over the sugar spheres loaded with Naltrexone HCl using a fluid bed coating machine. |
| 4. Retardant Coating | Prepare the non-release coating solution by mixing the Eudragit RS30D, Triethyl Citrate, Talc, and Purified Water. Apply this dispersion over the loaded and overcoated sugar spheres using a fluid bed coating machine. |
| 5. Overcoating | Prepare a second overcoating solution by dispersing Opadry White in Purified Water. Apply this dispersion over the nonrelease coated naltrexone spheres using a fluid bed coating machine |
| 6. Curing | Cure the spheres at 45° C. for approximately 48 hours. |

The multiparticulates of Example 1 can be modified in order to have an amount of naltrexone released which provides a desired pharmacological effect as disclosed herein.

Example 2

In Example 2, a substantially non-releasable form of an opioid antagonist (naltrexone HCl) is prepared as naltrexone HCl containing granulates. The granulates are comprised of naltrexone HCl dispersed in a matrix that renders the antagonist substantially non-releasable.

Formula:

| Ingredient | Amt/unit (mg) |
|---|---|
| Naltrexone HCl | 5.0 |
| Dicalcium Phosphate | 53.0 |
| Poly (DI-Lactide-Co-Glycolide) polymer (PLGA) MW ~100,000 | 12.0 |
| Ethyl Acetate | |
| Total | 70.0 |

*Used as a vehicle for application of PLGA polymer.

Process:

| 1. Solution Preparation | Dissolve PLGA in Ethyl Acetate by mixing. |
|---|---|
| 2. Granulation | Place the Naltrexone HCl, and Dicalcium Phosphate in a fluid bed coating machine and granulate by spraying the above solution. |

The multiparticulates of Example 2 can be modified in order to have an amount of naltrexone released which provides a desired pharmacological effect as disclosed herein.

Example 3

In Example 3, a substantially non-releasable form of an opioid antagonist (naltrexone HCl) is prepared as naltrexone HCl extruded pellets.

Formula:

| Ingredient | Amt/unit (mg) |
| --- | --- |
| Naltrexone HCl | 5.0 |
| Eudragit RSPO | 180.0 |
| Stearyl Alcohol | 55.0 |
| Total | 240.0 |

Process:

| 1. Milling | Pass stearyl alcohol flakes through an impact mill. |
| --- | --- |
| 2. Blending | Mix Naltrexone HCl, Eudragit, and milled Stearyl Alcohol in a twin shell blender. |
| 3. Extrusion | Continuously feed the blended material into a twin screw extruder and collect the resultant strands on a conveyor. |
| 4. Cooling | Allow the strands to cool on the conveyor. |
| 5. Pelletizing | Cut the cooled strands into pellets using a Pelletizer. |
| 6. Screening | Screen the pellets and collect desired sieve portion. |

The multiparticulates of Example 3 can be modified in order to have an amount of naltrexone Released which provides a desired pharmacological effect as disclosed herein Example 4

Hydrocodone Bitartrate Controlled Release Tablets with Naltrexone HCl Beads and Releasable Naltrexone

| Ingredient | Amt/unit (mg) |
| --- | --- |
| Hydrocodone Bitartrate | 30.0 |
| Stearyl Alcohol | 44.0 |
| Anhydrous Dicalcium Phosphate (Powdered) | 62.0 |
| Microcrystalline Cellulose | 62.0 |
| Glyceryl Behenate | 20.0 |
| Naltrexone HCl Beads (Example 1) | 84.0 |
| Magnesium Stearate | 2.0 |
| Opadry Red | 10.0 |
| Purified Water | 56.7* |
| Total | 314.0 |

*Remains in product as residual moisture only.

Process:

| 1. Milling | Pass the Stearyl Alcohol flakes through an occillating mill. |
| --- | --- |
| 2. Blending | Mix the Hydrocodone Bitartrate, milled Stearyl Alcohol, Anhydrous Dicalcium Phosphate, Microcrystalline Cellulose, and Glyceryl Behenate in a twin shell blender. |
| 3. Extrusion | Continuously feed the blended material into a twin screw extruder and collect the resultant heated material on a conveyor. |
| 4. Cooling | Allow the extrudate to cool on the conveyor. |
| 5. Milling | Mill the cooled extrudate using an occillating mill. |
| 6. Blending | Blend the milled extrudate, naltrexone HCl beads (from Example 1), and Magnesium Stearate. |
| 7. Compression | Compress the resultant granulation using a tablet press. |
| 8. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an an amount to have a desired pharmacological effect as disclosed herein and can be immediate or sustained release.

Example 5

Hydrocodone Bitartrate Controlled Release Tablets with Naltrexone HCl Granulation

| Ingredient | Amt/unit (mg) |
| --- | --- |
| Hydrocodone Bitartrate | 30.0 |
| Stearyl Alcohol | 44.0 |
| Anhydrous Dicalcium Phosphate (Powdered) | 62.0 |
| Microcrystalline Cellulose | 62.0 |
| Glyceryl Behenate | 20.0 |
| Naltrexone HCl Granulation (Example 2) | 70.0 |
| Magnesium Stearate | 2.0 |
| Opadry Red | 10.0 |
| Purified Water | 56.7* |
| Total | 300.0 |

*Remains in product as residual moisture only.

Process:

| 1. Milling | Pass the Stearyl Alcohol flakes through an occillating mill. |
| --- | --- |
| 2. Blending | Mix the Hydrocodone Bitartrate, milled Stearyl Alcohol, Anhydrous Dicalcium Phosphate, Microcrystalline Cellulose, and Glyceryl Behenate in a twin shell blender. |
| 3. Extrusion | Continuously feed the blended material into a twin screw extruder and collect the resultant heated material on a conveyor. |
| 4. Cooling | Allow the extrudate to cool on the conveyor. |
| 5. Milling | Mill the cooled extrudate using an occillating mill. |
| 6. Blending | Blend the milled extrudate, Naltrexone HCl granulation (from Example 2), and Magnesium Stearate. |
| 7. Compression | Compress the resultant granulation using a tablet press. |
| 8. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 6

Oxycodone HCl Controlled Release Tablets with Naltrexone HCl Beads

| Ingredient | Amt/unit (mg) |
| --- | --- |
| Oxycodone HCl | 20.00 |
| Spray Dried Lactose | 59.25 |
| Povidone | 5.00 |
| Eudragit RS 30D (dry wt.) | 10.00 |
| Triacetin | 2.00 |
| Stearyl Alcohol | 25.00 |
| Talc | 2.50 |
| Magnesium Stearate | 1.25 |
| Naltrexone HCl Beads (Example 1) | 84.00 |
| Opadry Pink | 6.00 |
| Purified Water | 34.00* |
| Total | 215.00 |

*Remains in product as residual moisture only.

Process:

| 1. Solution Preparation | Plasticize the Eudragit with Triacetin by mixing. |
| --- | --- |
| 2. Granulation | Place Oxycodone HCl, Spray Dried Lactose, and Povidone into a fluid bed granulator and apply the above solution. |
| 3. Milling | Pass the granulation through a rotating impeller mill. |
| 4. Drying | Dry granulation if moisture content is too high. |
| 5. Waxing | Melt Stearyl Alcohol and wax the above granulation by adding melted Stearyl Alcohol onto granulation while mixing. |
| 6. Cooling | Cool the waxed granulation in a fluid bed dryer. |
| 7. Milling | Pass the cooled waxed granulation through a rotating impeller mill. |
| 8. Blending | Blend the milled waxed granulation, Talc, Magnesium Stearate, and Naltrexone HCl beads (from Example 1). |
| 9. Compression | Compress the resultant granulation using a tablet press. |
| 10. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an an amount to have a desired pharmacological effect as disclosed herein and can be immediate or sustained release.

Example 7

Oxcodone HCl Controlled Release Tablets with Naltrexone HCl Granulation

| Ingredient | Amt/unit (mg) |
| --- | --- |
| Oxycodone HCl | 20.00 |
| Spray Dried Lactose | 59.25 |
| Povidone | 5.00 |
| Eudragit RS 30D (dry wt.) | 10.00 |
| Triacetin | 2.00 |
| Stearyl Alcohol | 25.00 |
| Talc | 2.50 |
| Magnesium Stearate | 1.25 |
| Naltrexone HCl Granulation (Example 2) | 70.00 |
| Opadry Pink | 6.00 |
| Purified Water | 34.00* |
| Total | 201.00 |

*Remains in product as residual moisture only.

Process:

| 1. Solution Preparation | Plasticize the Eudragit with Triacetin by mixing. |
| --- | --- |
| 2. Granulation | Place Oxycodone HCl, Spray Dried Lactose and Povidone into a fluid bed granulator and apply the above solution. |
| 3. Milling | Pass the granulation through a rotating impeller mill. |
| 4. Drying | Dry granulation if moisture content is too high. |
| 5. Waxing | Melt Stearyl Alcohol and wax the above granulation by adding melted Stearyl Alcohol onto granulation while mixing. |
| 6. Cooling | Cool the waxed granulation in a fluid bed dryer. |
| 7. Milling | Pass the cooled waxed granulation through a rotating impeller mill. |
| 8. Blending | Blend the milled waxed granulation, Talc, Magnesium Stearate, and Naltrexone HCl granulation (from Example 2). |
| 9. Compression | Compress the resultant granulation using a tablet press. |
| 10. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an an amount to have a desired pharmacological effect as disclosed herein and can be immediate or sustained release.

Example 8

Hydromorphone HCl Controlled Release Capsules with Naltrexone HCl Extruded Pellets Formula:

| Ingredient | Amt/unit (mg) |
| --- | --- |
| Hydromorphone HCl | 12.0 |
| Eudragit RSPO | 76.5 |
| Ethylcellulose | 4.5 |
| Stearyl Alcohol | 27.0 |
| Naltrexone HCl Pellets (Example 3) | 240.0 |
| Hard Gelatin Capsules | √ |
| Total | 360.0 |

Process:

| | |
|---|---|
| 1. Milling | Pass Stearyl Alcohol flakes through an impact mill. |
| 2. Blending | Mix Hydromorphone HCl, Eudragit, Ethycellulose and milled Stearyl Alcohol in a twin shell blender. |
| 3. Extrusion | Continuously feed the blended material into a twin screw extruder and collect the resultant strands on a conveyor. |
| 4. Cooling | Allow the strands to cool on the conveyor. |
| 5. Pelletizing | Cut the cooled strands into pellets using a Pelletizer. |
| 6. Screening | Screen the pellets and collect desired sieve portion. |
| 7. Encapsulation | Fill the extruded Hydromorphone HCl pellets at 120 mg and Naltrexone HCl pellets (from Example 3) at 240 mg into hard gelatin capsules. |

The releasable naltrexone can be a) overcoated onto the pellets by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 9

Hydrocodone Bitartrate Controlled Release Tablets with Naltrexone HCl Beads

| Ingredient | Amt/unit (mg) |
|---|---|
| Hydrocodone Bitartrate | 30.0 |
| Stearyl Alcohol | 44.0 |
| Anhydrous Dicalcium Phosphate (Powdered) | 62.0 |
| Microcrystalline Cellulose | 62.0 |
| Glyceryl Behenate | 20.0 |
| Naltrexone HCl Beads (Example 1) | 84.0 |
| Magnesium Stearate | 2.0 |
| Opadry Red | 10.0 |
| Purified Water | 56.7* |
| Total | 314 |

*Remains in product as residual moisture only.

Process:

| | |
|---|---|
| 1. Milling | Pass the Stearyl Alcohol flakes through an occillating mill. |
| 2. Blending | Mix the Hydrocodone Bitartrate, milled Stearyl Alcohol, Anhydrous Dicalcium Phosphate, Microcrystalline Cellulose, and Glyceryl Behenate in a twin shell blender. |
| 3. Extrusion | Continuously feed the blended material into a twin screw extruder and collect the resultant heated material on a conveyor. |
| 4. Cooling | Allow the extrudate to cool on the conveyor. |
| 5. Milling | Mill the cooled extrudate using an occillating mill. |
| 6. Blending | Blend the milled extrudate, Naltrexone HCl beads (from Example 1), and Magnesium Stearate. |
| 7. Compression | Compress the resultant granulation using a tablet press. |
| 8. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 10

Hydrocodone Bitartrate Controlled Release Tablets with Naltrexone HCl Granulation

| Ingredient | Amt/unit (mg) |
|---|---|
| Hydrocodone Bitartrate | 30.0 |
| Stearyl Alcohol | 44.0 |
| Anhydrous Dicalcium Phosphate (Powdered) | 62.0 |
| Microcrystalline Cellulose | 62.0 |
| Glyceryl Behenate | 20.0 |
| Naltrexone HCl Granulation (Example 2) | 70.0 |
| Magnesium Stearate | 2.0 |
| Opadry Red | 10.0 |
| Purified Water | 56.7* |
| Total | 300.5 |

*Remains in product as residual moisture only.

Process:

| | |
|---|---|
| 1. Milling | Pass the Stearyl Alcohol flakes through an occillating mill. |
| 2. Blending | Mix the Hydrocodone Bitartrate, milled Stearyl Alcohol, Anhydrous Dicalcium Phosphate, Microcrystalline Cellulose, and Glyceryl Behenate in a twin shell blender. |
| 3. Extrusion | Continuously feed the blended material into a twin screw extruder and collect the resultant heated material on a conveyor. |
| 4. Cooling | Allow the extrudate to cool on the conveyor. |
| 5. Milling | Mill the cooled extrudate using an occillating mill. |
| 6. Blending | Blend the milled extrudate, Naltrexone HCl granulation (from Example 2), and Magnesium Stearate. |
| 7. Compression | Compress the resultant granulation using a tablet press. |
| 8. Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an an amount to have a desired pharmacological effect as disclosed herein and can be immediate or sustained release.

Example 11

Oxycodone HCl Controlled Release Tablets with Naltrexone HCl Beads

| Ingredient | Amt/unit (mg) |
|---|---|
| Oxycodone HCl | 20.00 |
| Spray Dried Lactose | 58.75 |
| Povidone | 5.00 |
| Eudragit RS 30D (dry wt.) | 10.00 |
| Triacetin | 2.00 |
| Stearyl Alcohol | 25.00 |

-continued

| Ingredient | Amt/unit (mg) |
|---|---|
| Talc | 2.50 |
| Magnesium Stearate | 1.25 |
| Naltrexone HCl Beads (Example 1) | 84.00 |
| Opadry Pink | 6.00 |
| Purified Water | 34.00* |
| Total | 215.00 |

*Remains in product as residual moisture only.

Process:

| | | |
|---|---|---|
| 1. | Solution Preparation | Plasticize the Eudragit with Triacetin by mixing. |
| 2. | Granulation | Place Oxycodone HCl, Spray Dried Lactose, and Povidone into a fluid bed granulator and apply the above solution. |
| 3. | Milling | Pass the granulation through a rotating impeller mill. |
| 4. | Drying | Dry granulation if moisture content is too high. |
| 5. | Waxing | Melt Stearyl Alcohol and wax the above granulation by adding melted Stearyl Alcohol onto granulation while mixing. |
| 6. | Cooling | Cool the waxed granulation in a fluid bed dryer. |
| 7. | Milling | Pass the cooled waxed granulation through a rotating impeller mill. |
| 8. | Blending | Blend the milled waxed granulation, Talc, Magnesium Stearate, and Naltrexone HCl beads (from Example 1). |
| 9. | Compression | Compress the resultant granulation using a tablet press. |
| 10. | Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 12

Oxycodone HCl Controlled Release Tablets with Naltrexone HCl Granulation

| Ingredient | Amt/unit (mg) |
|---|---|
| Oxycodone HCl | 20.00 |
| Spray Dried Lactose | 58.75 |
| Povidone | 5.00 |
| Eudragit RS 30D (dry wt.) | 10.00 |
| Triacetin | 2.00 |
| Stearyl Alcohol | 25.00 |
| Talc | 2.50 |
| Magnesium Stearate | 1.25 |
| Naltrexone HCl Granulation (Example 2) | 70.00 |
| Opadry Pink | 6.00 |
| Purified Water | 34.00* |
| Total | 201.00 |

*Remains in product as residual moisture only.

Process:

| | | |
|---|---|---|
| 1. | Solution Preparation | Plasticize the Eudragit with Triacetin by mixing. |
| 2. | Granulation | Place Oxycodone HCl, Spray Dried Lactose, and Povidone into a fluid bed granulator and apply the above solution. |
| 3. | Milling | Pass the granulation through a rotating impeller mill. |
| 4. | Drying | Dry granulation if moisture content is too high. |
| 5. | Waxing | Melt Stearyl Alcohol and wax the above granulation by adding melted Stearyl Alcohol onto granulation while mixing. |
| 6. | Cooling | Cool the waxed granulation in a fluid bed dryer. |
| 7. | Milling | Pass the cooled waxed granulation through a rotating impeller mill. |
| 8. | Blending | Blend the milled waxed granulation, Talc, Magnesium Stearate, and Naltrexone HCl granulation (from Example 2). |
| 9. | Compression | Compress the resultant granulation using a tablet press. |
| 10. | Coating | Prepare a film coating solution by dispersing the Opadry in Purified Water and applying it to the tablet cores. |

The releasable naltrexone can be a) overcoated onto the tablet by e.g., including it in the Opadry solution, b) modifying the sequestered component to release the desired naltrexone, c) including the naltrexone with the opioid agonist; or included in any other method known in the art. The amount of naltrexone should be in an an amount to have a desired pharmacological effect as disclosed herein and can be immediate or sustained release.

Example 13

Hydromorphone HCl Controlled Release Capsules with Naltrexone HCl Extruded Pellets
Formula:

| Ingredient | Amt/unit (mg) |
|---|---|
| Hydromorphone HCl | 12.0 |
| Eudragit RSPO | 76.0 |
| Ethylcellulose | 4.5 |
| Stearyl Alcohol | 27.0 |
| Naltrexone HCl Pellets (Example 3) | 240.0 |
| Hard Gelatin Capsules | √ |
| Total | 360.0 |

Process:

| | | |
|---|---|---|
| 1. | Milling | Pass stearyl alcohol flakes through an impact mill. |
| 2. | Blending | Mix Hydromorphone HCl, Eudragit, Ethycellulose and milled Stearyl Alcohol in a twin shell blender. |
| 3. | Extrusion | Continuously feed the blended material into a twin screw extruder and collect the resultant strands on a conveyor. |
| 4. | Cooling | Allow the strands to cool on a Conveyor. |
| 5. | Pelletizing | Cut the cooled strands into pellets using a Pelletizer. |
| 6. | Screening | Screen the pellets and collect desired sieve portion. |
| 7. | Encapsulation | Fill the extruded Hydromorphone HCl pellets at 120.0 mg and Naltrexone HCl pellets (from Example 3) at 240 mg into hard gelatin capsules. |

The releasable naltrexone can be a) overcoated onto the pellets by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 14

Sequestered Naltrexone HCl Beads

In Example 14, Naltrexone HCl beads for incorporation into capsules were prepared having the following formulation in Table 14 below.

TABLE 14

| | Ingredients | Amt/unit (mg) |
|---|---|---|
| Step 1. Drug layering | Naltrexone HCl | 2.1 |
| | Non-pareil beads (30/35 mesh) | 39.98 |
| | Opadry Clear (Hydroxypropymethyl cellulose) | 0.4 |
| | Sodium ascorbate | 0.027 |
| | Ascorbic acid | 0.05 |
| Step 2. Anionic polymer coat | Eudragit L30D (dry) | 2.164 |
| | Triethyl Citrate | 0.433 |
| | Cabosil | 0.108 |
| Step 3. Sustained release coat | Eudragit RS30D (dry) | 17.475 |
| | Triethyl citrate | 3.495 |
| | Cabosil | 0.874 |
| Step 4. Seal coat | Opadry Clear (Hydroxypropylmethyl cellulose) | 1.899 |
| | Cabosil | 0.271 |
| Total (on dry basis) | | 69.287 |

Process:
1. Dissolve naltrexone HCl, ascorbic acid, sodium ascorbate and Opadry Clear in water. Spray the drug solution onto non-pareil beads in a fluid bed coater with Wurster insert.
2. Disperse Eudragit L30D, Triethyl citrate, and Cabosil in water. Spray the dispersion onto the drug-loaded beads in the fluid bed coater.
3. Disperse Eudragit RS30D, triethyl citrate, and Cabosil in water. Spray the dispersion onto the beads in the fluid bed coater.
4. Dissolve Opadry Clear in water. Spray the solution onto the beads in the fluid bed coater.
5. Cure the beads at 60° C. for 24 hours.

Example 15

Sequestered Naltrexone Multiparticulates

A naltrexone melt extruded multiparticulate formulation was prepared. The melt extruded multiparticulate formulation is listed in Table 15 below.

TABLE 15

| Ingredients | Amt/Unit (mg) |
|---|---|
| Naltrexone HCl | 2.0 |
| Eudragit RSPO | 88.0 |
| Stearyl alcohol | 15.0 |
| Stearic acid | 15.0 |
| BHT | 1.0 |
| Total | 121.0 |

Process:
1. Blend milled Stearic acid, stearyl alcohol, Naltrexone HCl, BHT, and Eudragit RSPO using a V-blender.
2. Extrude the mixture using a Powder Feeder, Melt Extruder (equipped with the 6×1 mm die head), Conveyor, Lasermike, and Pelletizer.
   Powder feed rate—4.2 kg/hr; vacuum—980 mBar
   Conveyor—such that diameter of extrudate is 1 mm
   Pelletizer—such that pellets are cut to 1 mm in length
3. Screen pellets using #16 mesh and #20 mesh screens. Collect material that passes through the #16 mesh screen and is retained on the #20 mesh screen.
4. Fill size #2 clear gelatin capsules with the pellets. Range: NLT 114 mg and NMT 126 mg.

Example 16

Sequestered Naltrexone CR Beads

A naltrexone sustained release bead formulation was prepared which can be incorporated into an opioid controlled release granulation and compressed into tablets. The naltrexone controlled release bead formulation is listed in Table 16 below.

TABLE 16

| | Ingredients | Amt/unit* (mg) |
|---|---|---|
| Step 1. Drug layering | Naltrexone HCl | 0.609 |
| | Non-pareil beads (30/35 mesh) | 67.264 |
| | Opadry Clear | 0.547 |
| Step 2. Seal coat | Eudragit L | 2.545 |
| | Triethyl citrate | 0.636 |
| | Glyceryl monostearate | 0.239 |
| Step 3. Sustained release coat | Eudragit RS30D (dry) | 43.789 |
| | Triethyl citrate | 8.758 |
| | Cabosil | 2.189 |
| Step 4. Seal coat | Opadry Clear (Hydroxypropylmethyl cellulose) | 2.053 |
| | Cabosil | 1.368 |
| Total | | 130 |

Process:
1. Dissolve naltrexone HCl and Opadry (HPMC) in water. Spray the drug solution onto non-pareil beads in a fluid bed coater with Wurster insert.
2. Disperse Eudragit L, Triethyl citrate, and glyceryl monostearate in water. Spray the dispersion onto the drug-loaded beads in the fluid bed coater.
3. Disperse Eudragit RS, triethyl citrate, and Cabosil in water. Spray the dispersion onto the beads in the fluid bed coater.
4. Dissolve Opadry in water. Spray the solution onto the beads in the fluid bed coater.
5. Cure the beads at 60° C. for 24 hours.

Example 17

Controlled Release Oxycodone 20 mg

In Example 17, a sustained release 20 mg oxycodone formulation was prepared having the formulation listed in Table 17 below.

TABLE 17

| Ingredients | Amt/Unit (mg) |
|---|---|
| Oxycodone HCl | 20.0 |
| Spray Dried Lactose | 59.25 |
| Povidone | 5.0 |
| Eudragit RS30D (solids) | 10.0 |
| Triacetin | 2.0 |
| Stearyl Alcohol | 25.0 |

TABLE 17-continued

| Ingredients | Amt/Unit (mg) |
|---|---|
| Talc | 2.5 |
| Magnesium Stearate | 1.25 |
| Opadry Pink Y-S-14518A | 4.0 |
| Total | 129.0 |

Process:
1. Granulation: Spray the Eudragit/Triacetin dispersion onto the Oxycodone HCl, Spray Dried Lactose and Povidone using a fluid bed granulator.
2. Milling: Discharge the granulation and pass through a mill.
3. Waxing: Melt the stearyl alcohol and add to the milled granulation using a mixer. Allow to cool.
4. Milling: Pass the cooled granulation through a mill.
5. Lubrication: Lubricate the granulation with talc and magnesium stearate using a mixer.
6. Compression: Compress the granulation into tablets using a tablet press.
7. Film coating: Apply an aqueous film coat to the tablets.

Example 18

In Example 18, naltrexone beads prepared in accordance with Example 16 are incorporated into the sustained release 20 mg oxycodone tablets prepared in accordance with Example 17 and having the formula listed in Table 18 below.

TABLE 18

| | Ingredients | Amt/unit* (mg) |
|---|---|---|
| Step 1. Granulation | Oxycodone HCl | 20.0 |
| | Spray Dried Lactose | 59.25 |
| | Povidone | 5.0 |
| | Eudragit RS30D (dry) | 10.0 |
| | Triacetin | 2.0 |
| | Stearyl alcohol | 25.0 |
| | Talc | 2.5 |
| | Magnesium | 1.25 |
| Step 2. Combination tablet | OxyContin granulation (Example 3) | 125 |
| | Naltrexone CR beads (Formula 2) | 140 |

Process:
1. Spray the Eudragit/triacetin dispersion onto the Oxycodone HCl, spray dried lactose and povidone using a fluid bed granulator.
2. Discharge the granulation and pass through a mill.
3. Melt the stearyl alcohol and add to the milled granulation using a mill. Allow to cool.
4. Pass the cooled granulation through a mill.
5. Lubricate the granulation with talc and magnesium stearate. Using a mixer.
6. Mix naltrexone beads with the above granulation and compress into tablets.

Alternate Process:
1. Spray the Eudragit/triacetin dispersion onto the Oxycodone HCl, spray dried lactose and povidone using a fluid bed granulator.
2. Discharge the granulation and pass through a mill.
3. Mix naltrexone beads (example 2) with the above granulation in a Hobar mixer.
4. Melt the stearyl alcohol and add to the above mixture. Allow to cool.
5. Pass the cooled granulation through a mill.
6. Lubricate the granulation with talc and magnesium stearate using a mixer.
7. Compress into tablets.

Releasable naltrexone can be a) overcoated onto the tablets by e.g., including it in the Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 19

Controlled Release Hydrocodone

A sustained release hydrocodone formulation was prepared having the formula in Table 19 below.

TABLE 19

| Ingredients | Amt/Unit (mg) | Amt/Batch (g) |
|---|---|---|
| Hydrocodone Bitartrate | 15.0 | 320.0 |
| Eudragit RSPO | 76.0 | 1520.0 |
| Eudragit RLPO | 4.0 | 80.0 |
| Stearyl Alcohol | 25.0 | 500.0 |
| Total | 120.0 | 2400.0 |

Process:
1. Blend milled Stearyl Alcohol, Eudragit RLPO, Hydrocodone Bitartrate, and Eudragit RSPO using a Hobart Mixer.
2. Extrude the granulation using a Powder Feeder, Melt Extruder (equipped with the 6×1 mm die head), Conveyor, Lasermike, and Pelletizer.

Powder feed rate—40 g/min; vacuum—980 mBar

Conveyor-such that diameter of extrudate is 1 mm

Pelletizer-such that pellets are cut to 1 mm in length

3. Screen pellets using #16 mesh and #20 mesh screens. Collect material that passes through the #16 mesh screen and is retained on the #20 mesh screen.
4. Fill size #2 clear gelatin capsules with the pellets. Range: NLT (not less than) 114 mg and NMT (not more than) 126 mg.

The sequestered naltrexone formulation of Example 15 can be incorporated in a capsule with the hydrocodone pellets. Preferably, the sequestered naltrexone pellets are indistinguishable from the hydrocodone pellets.

Releasable naltrexone can be a) overcoated onto the pellets by e.g., including it in an Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 20

Controlled Release Oxycodone HCl Beads

A sustained release oxycodone HCl bead formulation was prepared having the formula in Table 20 below.

TABLE 20

| | Ingredients | Amt/unit* (mg) |
|---|---|---|
| Step 1. Drug layering | Oxycodone HCl | 10.5 |
| | Non-pareil beads (30/35 mesh) | 45.349 |
| | Opadry Clear | 2.5 |
| Step 2. Sustained release coat | Eudragit RS30D (dry) | 7.206 |
| | Eudragit RL30D (dry) | 0.379 |
| | Triethyl citrate | 1.517 |
| | Cabosil | 0.379 |
| Step 3. Seal coat | Opadry Clear (Hydroxypropylmethyl cellulose) | 1.899 |
| | Cabosil | 0.271 |
| Total | | 70.0 |

Process:
1. Dissolve oxycodone HCl and Opadry (HPMC) in water. Spray the drug solution onto non-pareil beads in a fluid bed coater with Wurster insert.
2. Disperse Eudragit RS, Eudragit RL, triethyl citrate, and Cabosil in water. Spray the dispersion onto the beads in the fluid bed coater.
3. Dissolve Opadry in water. Spray the solution onto the beads in the fluid bed coater.
4. Cure the beads at 60° C. for 24 hours.

The sequestered naltrexone formulation of Example 14 can be incorporated in a capsule with the oxycodone beads. Preferably, the sequestered naltrexone beads are indistinguishable from the oxycodone beads.

Releasable naltrexone can be a) overcoated onto the beads by e.g., including it in an Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

Example 21

Controlled Release Hydromorphone

A sustained release hydromorphone HCl formulation was prepared having the formula in Table 21 below:

TABLE 21

| Ingredients | Amt/Unit (mg) |
|---|---|
| Hydromorphone HCl | 12.0 |
| Eudragit RSPO | 76.5 |
| Ethocel | 4.5 |
| Stearic acid | 27.0 |
| Total | 120.0 |

Process:
1. Blend milled Stearic acid, ethocel, Hydrocodone Bitartrate, and Eudragit RSPO using a V-blender.
2. Extrude the mixture using a Powder Feeder, Melt Extruder (equipped with the 6×1 mm die head), Conveyor, Lasermike, and Pelletizer.
   Powder feed rate—4.2 kg/hr; vacuum—980 mBar
   Conveyor—such that diameter of extrudate is 1 mm
   Pelletizer—such that pellets are cut to 1 mm in length
3. Screen pellets using #16 mesh and #20 mesh screens. Collect material that passes through the #16 mesh screen and is retained on the #20 mesh screen.
4. Fill size #2 clear gelatin capsules with the pellets. Range: NLT 114 mg and NMT 126 mg.

The sequestered naltrexone formulation of Example 15 can be incorporated in a capsule with the hydromorphone pellets. Preferably, the sequestered naltrexone pellets are indistinguishable from the hydrocodone pellets.

Releasable naltrexone can be a) overcoated onto the pellets by e.g., including it in an Opadry solution, b) modifying the sequestered component to release the desired naltrexone, c) including the naltrexone with the opioid agonist; or included in any other method known in the art. The amount of naltrexone should be in an amount to have a desired pharmacological effect as disclosed herein and can be immediate or sustained release.

What is claimed is:

1. An oral dosage form comprising:
   (i) a therapeutically effective amount of an opioid agonist;
   (ii) an opioid antagonist in a releasable form; and
   (iii) an additional opioid antagonist combined with one or more pharmaceutically acceptable hydrophobic materials such that the additional opioid antagonist is sequestered in the dosage form which is administered orally intact,
   wherein the opioid antagonist in the releasable form is naltrexone or a pharmaceutically acceptable salt thereof,
   at least one of the hydrophobic materials comprises a cellulose polymer or an acrylic polymer,
   the additional opioid antagonist is selected from the group consisting of naloxone, nalmephene, cyclazocine, levallorphan, pharmaceutically acceptable salts thereof and mixtures thereof, and
   said one or more pharmaceutically acceptable hydrophobic materials separate the additional opioid antagonist from the opioid antagonist in the releasable form.

2. An oral dosage form comprising:
   (i) a first component comprising
      a therapeutically effective amount of an opioid agonist, and
      an opioid antagonist in a releasable form comprising naltrexone or a pharmaceutically acceptable salt thereof; and
   (ii) a second component comprising an additional opioid antagonist combined with one or more pharmaceutically acceptable hydrophobic materials such that the additional opioid antagonist is sequestered in the dosage form which is administered orally intact, wherein
      at least one of the hydrophobic materials comprises a cellulose polymer or an acrylic polymer,
      the additional opioid antagonist is selected from the group consisting of naloxone, nalmephene, cyclazocine, levallorphan, pharmaceutically acceptable salts thereof and mixtures thereof, and
      said one or more pharmaceutically acceptable hydrophobic materials separate the additional opioid antagonist from the opioid antagonist in the releasable form.

3. The dosage form of claim 1, further comprising a sustained release excipient which provides a sustained release of the opioid agonist and the opioid antagonist in the releasable form.

4. The dosage form of claim 1, wherein the additional opioid antagonist is in the form of multiparticulates individually coated with said one or more pharmaceutically acceptable hydrophobic materials.

5. The dosage form of claim 1, wherein the additional opioid antagonist is dispersed in a matrix comprising said one or more pharmaceutically acceptable hydrophobic materials.

6. The dosage form of claim 1, wherein the additional opioid antagonist is naloxone or a pharmaceutically acceptable salt thereof.

7. The dosage form of claim 1, wherein the additional opioid antagonist is combined with said one or more pharmaceutically acceptable hydrophobic materials such that the intact dosage form releases not more than 5% of the additional opioid antagonist at 1 hour, and the tampered dosage form releases at least 15% of the additional opioid antagonist at 1 hour, based on the dissolution at 1 hour of the dosage form in 900 ml of Simulated Gastric Fluid using a USP Type II (paddle) apparatus at 75 rpm at 37° C.

8. The dosage form of claim 2, wherein the additional opioid antagonist is combined with said one or more pharmaceutically acceptable hydrophobic materials such that the intact dosage form releases not more than 5% of the additional antagonist at 1 hour, and the tampered dosage form releases at least 15% of the additional antagonist at 1 hour, based on the dissolution at 1 hour of the dosage form in 900 ml of Simulated Gastric Fluid using a USP Type II (paddle) apparatus at 75 rpm at 37° C.

9. The dosage form of claim 1, wherein the opioid antagonist in the releasable form is the pharmaceutically acceptable salt of naltrexone.

10. The dosage form of claim 2, wherein the opioid antagonist in the releasable form comprises the pharmaceutically acceptable salt of naltrexone.

11. The dosage form of claim 10, wherein the opioid agonist is oxycodone or a pharmaceutically acceptable salt thereof.

12. The dosage form of claim 1, wherein the additional opioid antagonist is included in an effective amount to block the euphoric effect of the opioid agonist when the dosage form is administered orally after tampering.

13. The dosage form of claim 2, wherein the additional opioid antagonist is included in an effective amount to block the euphoric effect of the opioid agonist when the dosage form is administered orally after tampering.

14. A method of treating pain comprising administering to a subject in need of said treatment a dosage form according to claim 1 or a dosage form according to claim 2.

15. The method of claim 14, wherein the dosage form according to claim 1 is administered to said subject.

16. The dosage form of claim 1, said one or more pharmaceutically acceptable hydrophobic materials separate the opioid agonist from the opioid antagonist in the releasable form.

17. The dosage form of claim 2, said one or more pharmaceutically acceptable hydrophobic materials separate the opioid agonist from the opioid antagonist in the releasable form.

* * * * *